(12) United States Patent
Amparo et al.

(10) Patent No.: US 8,541,391 B2
(45) Date of Patent: Sep. 24, 2013

(54) CRYSTALLINE PHASES OF 5,6-DICHLORO-2-(ISOPROPYLAMINO)-1-β-L-RIBOFURANOSYL-1H-BENZIMIDAZOLE

(75) Inventors: Eugene C. Amparo, Malvern, PA (US); Cristina Stoica, Almere (NL); Mihaela Pop, Amsterdam (NL); Jaroslaw Mazurek, Delft (NL)

(73) Assignee: ViroPharma Incorporated, Exton, PA (US)

( * ) Notice: Subject to any disclaimer, the term of this patent is extended or adjusted under 35 U.S.C. 154(b) by 54 days.

(21) Appl. No.: 13/282,504

(22) Filed: Oct. 27, 2011

(65) Prior Publication Data

US 2012/0277177 A1 Nov. 1, 2012

Related U.S. Application Data

(60) Provisional application No. 61/407,626, filed on Oct. 28, 2010.

(51) Int. Cl.
*A01N 43/04* (2006.01)
*A61K 31/70* (2006.01)

(52) U.S. Cl.
USPC ............ 514/46; 514/43; 514/45; 536/27.1; 536/27.13

(58) Field of Classification Search
None
See application file for complete search history.

(56) References Cited

U.S. PATENT DOCUMENTS

| | | | |
|---|---|---|---|
| 6,077,832 A | 6/2000 | Chamberlain et al. | |
| 6,469,160 B1 | 10/2002 | Glover et al. | |
| 6,482,939 B1 * | 11/2002 | Hodgson et al. | 536/28.9 |
| 2012/0178709 A1 | 7/2012 | Coquerel et al. | |
| 2012/0283210 A1 | 11/2012 | Peabody | |

OTHER PUBLICATIONS

Flack, H.D., "On Enantiomorph-Polarity Estimation", Acta. Cryst., A39: 876-881 (1983).

* cited by examiner

*Primary Examiner* — Patrick Lewis
(74) *Attorney, Agent, or Firm* — Patrick J. Hagan; Dann, Dorfman, Herrell and Skillman, P.C.

(57) ABSTRACT

The invention relates to novel crystalline forms of 5,6-dichloro-2-(isopropylamino)-1-(β-L-ribofuranosyl)-1H-benzimidazole (Maribavir), pharmaceutical compositions thereof and their use in medical therapy.

13 Claims, 30 Drawing Sheets

X-ray powder diffraction

X-ray powder diffraction

X-ray powder diffraction

X-ray powder diffraction

FIG. 15D1
Calculated X-ray powder diffraction (calculated from the single crystal data, Table 3; the experimental X-ray powder diffraction pattern is affected by significant preferred orientation effects)
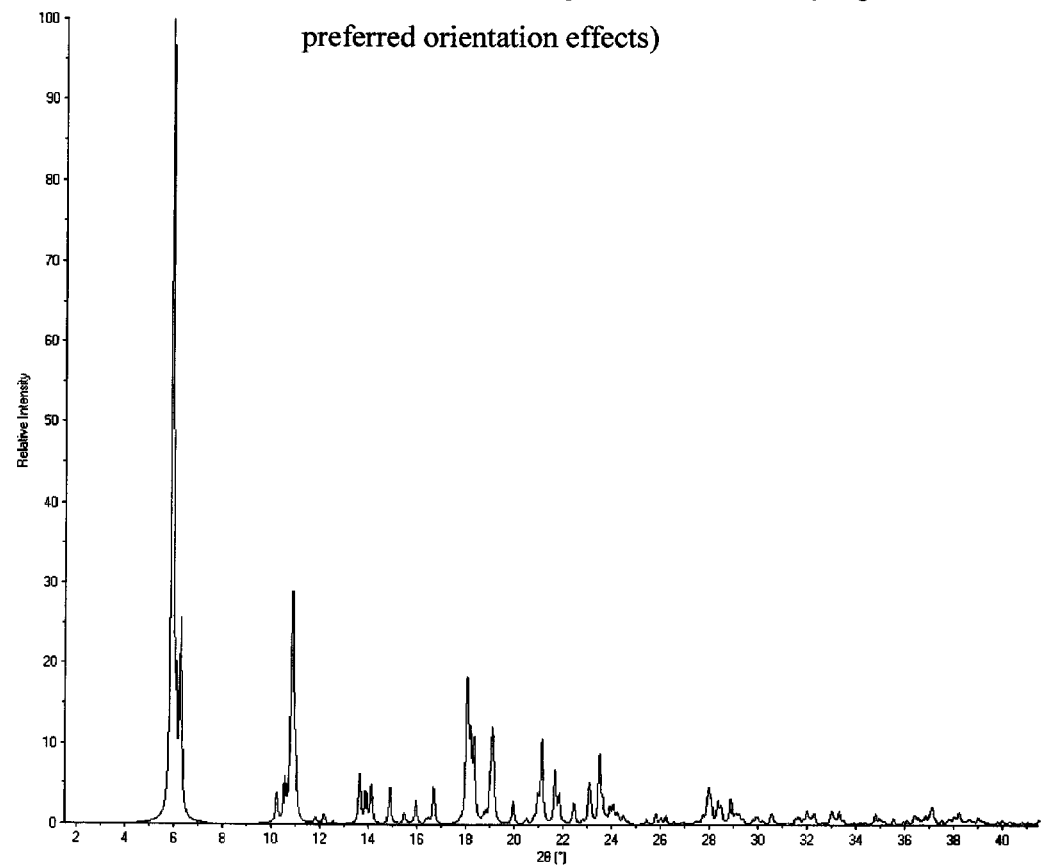

FIG. 15D2
X-ray powder diffraction (the experimental X-ray powder diffraction pattern is affected by significant preferred orientation effects)
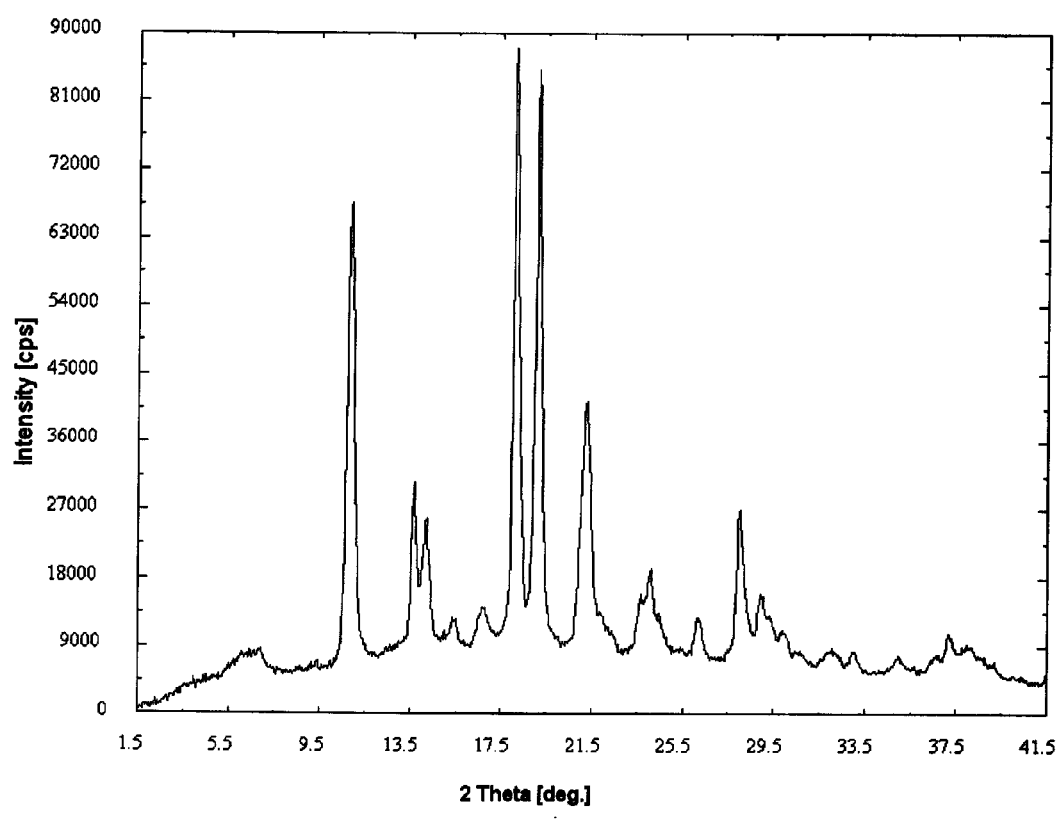

X-ray powder diffraction

X-ray powder diffraction

FIG. 15H1
Calculated X-ray powder diffraction (calculated from the single crystal data, Table 4; the experimental X-ray powder diffraction pattern is affected by significant preferred orientation effects)
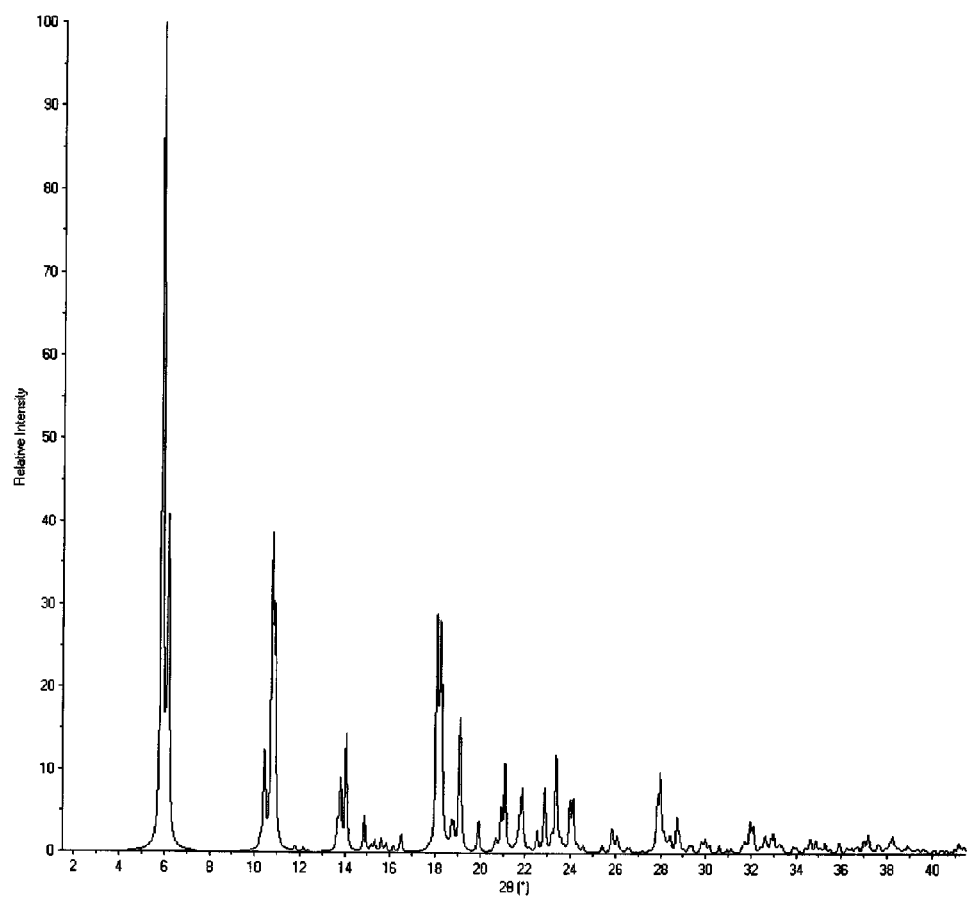

Fig. 15H2
X-ray powder diffraction (the experimental X-ray powder diffraction pattern is affected by significant preferred orientation effects)
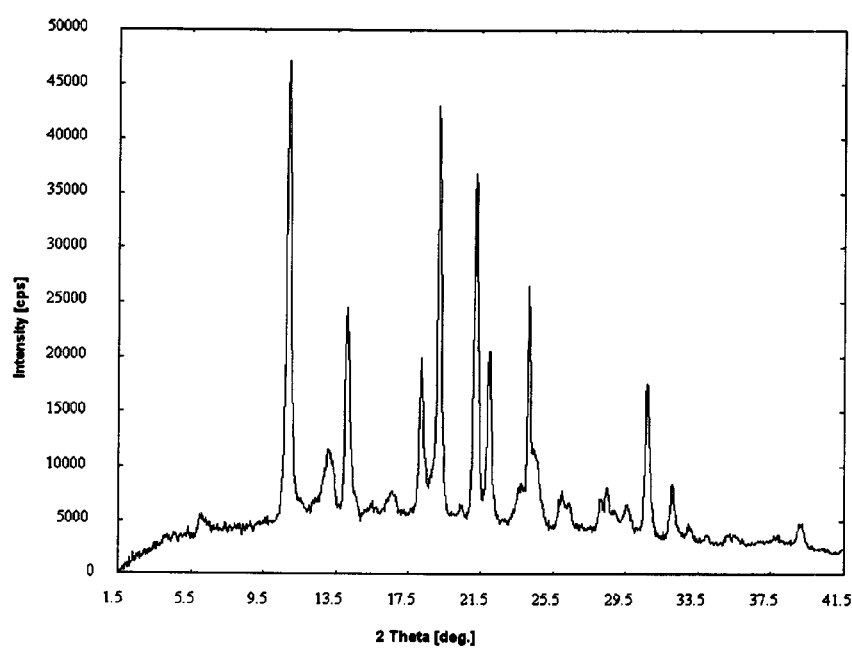

X-ray powder diffraction

X-ray powder diffraction

X-ray powder diffraction

CRYSTALLINE PHASES OF 5,6-DICHLORO-2-(ISOPROPYLAMINO)-1-β-L-RIBOFURANOSYL-1H-BENZIMIDAZOLE

CROSS-REFERENCE TO RELATED APPLICATIONS

The present application claims the benefit of U.S. Provisional Patent Application No. 61/407,626, filed Oct. 28, 2010, the entire disclosure of which is incorporated by reference herein.

BACKGROUND OF THE INVENTION

The present invention relates to an anhydrate crystalline form, hydrates and numerous other solvates of the antiviral compound 5,6-dichloro-2-(isopropylamino)-1-(β-L-ribofuranosyl)-1H-benzimidazole (also known as 1263 W94; a compound of formula (I), below), pharmaceutical formulations comprising such crystalline form and solvates, and their use in therapy.

5,6-dichloro-2-(isopropylamino)-1-(β-L-ribofuranosyl)-1H-benzimidazole (1263W94) is a benzimidazole derivative useful in medical therapy. U.S. Pat. No. 6,077,832 discloses 5,6-dichloro-2-(isopropylamino)-1-(β-L-ribofuranosyl)-1H-benzimidazole and its use for the treatment or prophylaxis of viral infections such as those caused by herpes viruses. The compound as disclosed in U.S. Pat. No. 6,077,832 is an amorphous, non-crystalline material.

The structure of 5,6-dichloro-2-(isopropylamino)-1-(β-L-ribofuranosyl)-1H-benzimidazole, a compound of formula (I) is shown below:

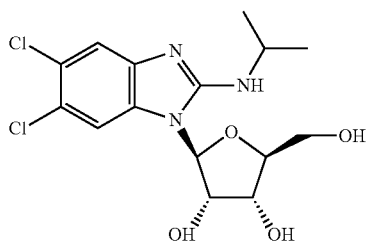 [SMILES: CC(C)Nc1nc2cc(Cl)c(Cl)cc2n1[C@H]1O[C@@H](CO)[C@H](O)[C@@H]1O]

The preparation of certain new crystalline forms and solvate forms of 5,6-dichloro-2-(isopropylamino)-1-(β-L-ribofuranosyl)-1H-benzimidazole, as well as pharmaceutical formulations thereof and their use in therapy are described in U.S. Pat. Nos. 6,469,160 and 6,482,939.

Different polymorphs normally have different solubilities, different residence times in the body and different therapeutic values. In view of these differences, it is important in drug development to determine the properties, and control, to the extent possible, the presence of polymorphs in any drug product administered in crystalline form that is submitted for regulatory approval.

SUMMARY OF THE INVENTION

It has now been discovered, in accordance with this invention, that 5,6-dichloro-2-(isopropylamino)-1-(β-L-ribofuranosyl)-1H-benzimidazole may be prepared in a novel anhydrate crystalline form, as well as hydrate and solvate forms in addition to those previously described.

According to one aspect of the invention there is provided the compound of formula (I) in a novel crystalline form, Form VIII. Form VIII is defined by the X-ray powder diffraction pattern illustrated in FIG. 1, which is obtained in the manner described in the examples that follow.

In another aspect of the invention various solvates of the compound of formula (I) are provided, which are selected from the group of methanol, ethyl formate, t-butylmethyl ether, acetonitrile, ethyl acetate, n-propyl acetate, isopropyl acetate, n-butyl acetate, isopropyl ether, 1,2-dimethoxyethane, toluene, 2,2-dimethyl-3-butanone, hexafluorbenzene, nitrobenzene, 1,4-dioxane, tetrahydrofuran (THF), n-heptane, cyclohexane, methylbutyrate solvates, or mixtures thereof. These solvates, which are defined by their respective X-ray powder diffraction patterns, illustrated in the accompanying Figures, are obtained using the procedures exemplified below.

In still another aspect of the present invention, pharmaceutical compositions are provided comprising one or more of the polymorphs described herein and a pharmaceutically acceptable carrier or excipient. Suitable carriers and excipients for the formulation of pharmaceutically acceptable compositions comprising the polymorphs of this invention are well known in the art and are disclosed, for example, in U.S. Pat. No. 6,077,832.

The present invention also provides a method for the treatment or prophylaxis of a viral infection, particularly a herpes infection, such as CMV infection, as well as disease caused by hepatitis B and hepatitis C viruses in a patient, e.g. a mammal such as a human, which comprises administering to the patient an effective antiviral amount of the compound of formula (I) as anhydrate crystalline Form VIII or a novel hydrate or solvate of such compound.

The present invention also includes the use of the compound of formula (I) in anhydrate crystalline Form VIII, hydrate and solvate forms in the preparation of a medicament for the treatment or prophylaxis of a viral infection.

In a further aspect of the invention, there is provided the compound of formula (I) as a mixture of any two or more of the anhydrate crystalline Form VIII, hydrates, or solvates described herein, or as a mixture with amorphous material or with one or more of the anhydrate crystalline forms and/or solvates previously described.

The novel crystalline Form VIII of the present invention is a useful intermediate for the preparation of maribavir Form VI as well as for preparing other anhydrate polymorphic and amorphous forms of maribavir. Form VIII has similar thermal behavior to Form VI, however, it may offer advantages over Form VI since it is obtained after a relatively short period of drying (Example 1) and without the formation of stable intermediate hydrates or solvates.

The compound of Formula I has a tendency to form hydrates and solvates. The new hydrates and solvates of the present invention are useful as intermediates in new processes for preparing the anhydrate forms. These processes involve dehydration and desolvation of the hydrates and solvates, by the steps of drying, storage and/or other techniques that might be applied in the production process of compound of formula (I).

The novel anhydrate crystalline Form VIII, hydrates and solvates described herein, which are characterized by their X-ray powder diffraction patterns (XRPD), thermogravimetric analysis (TGA) differencial scanning calorimetry (DSC) profiles, and IR spectral can be produced in various conventional solid and liquid dose forms for therapeutic use in the manner previously described in U.S. Pat. Nos. 6,469,160 and 6,482,939.

Figure 1:
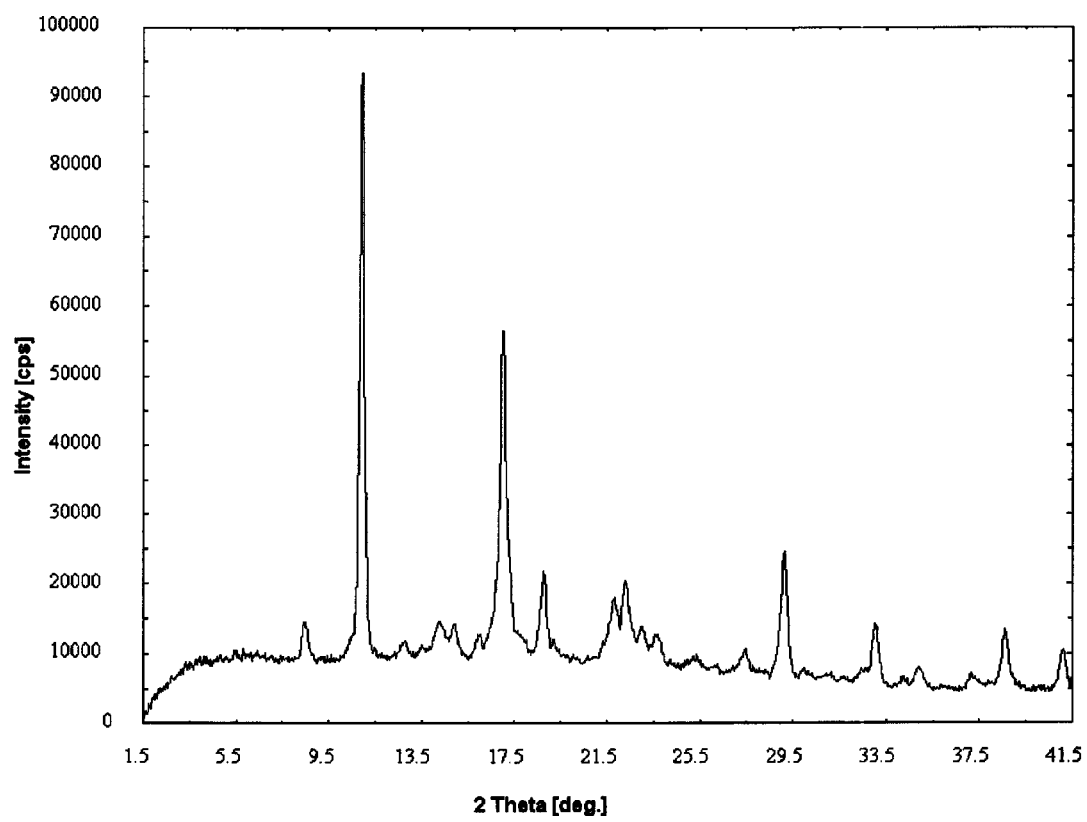
FIG. 1 sets forth identifying data for Form VIII of the compound of Formula I, above, including X-ray powder diffraction pattern.
Figure 2:
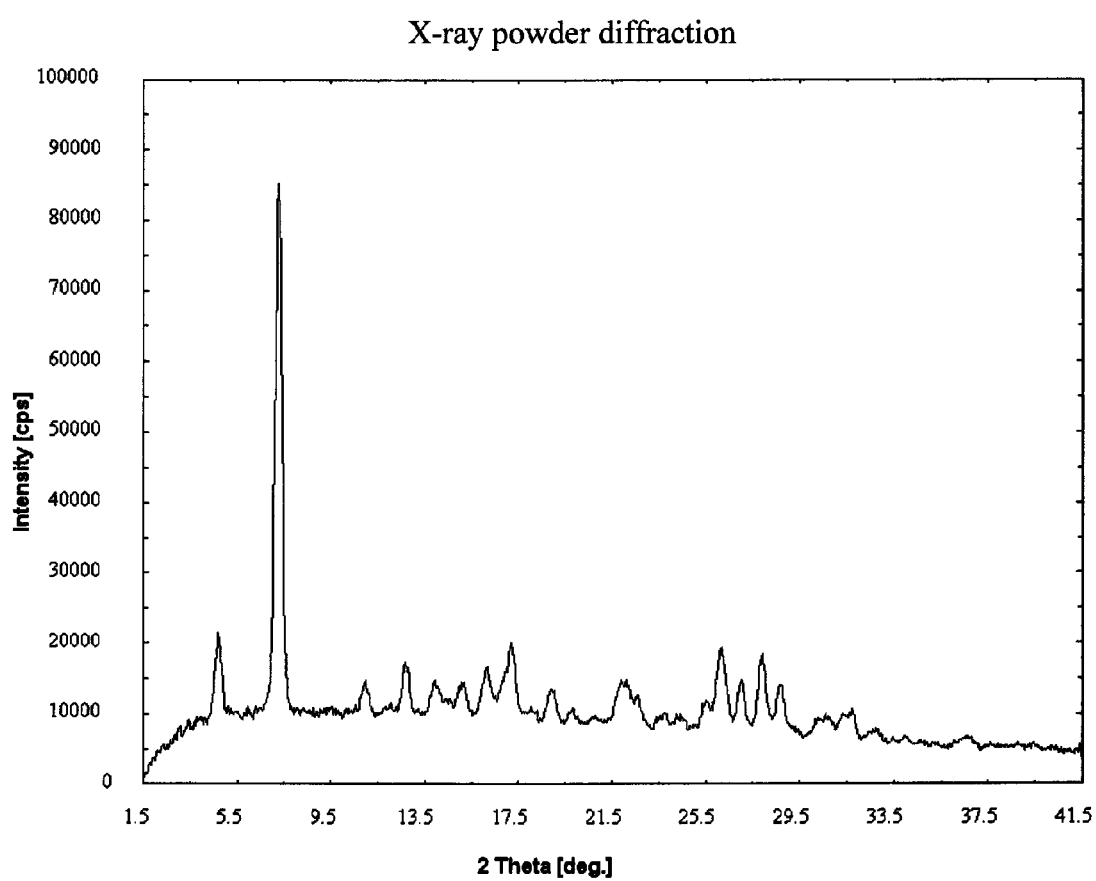
FIG. 2 sets forth identifying data for the dihyrate of the compound of Formula I, above, including X-ray powder diffraction pattern.
Figure 15A:
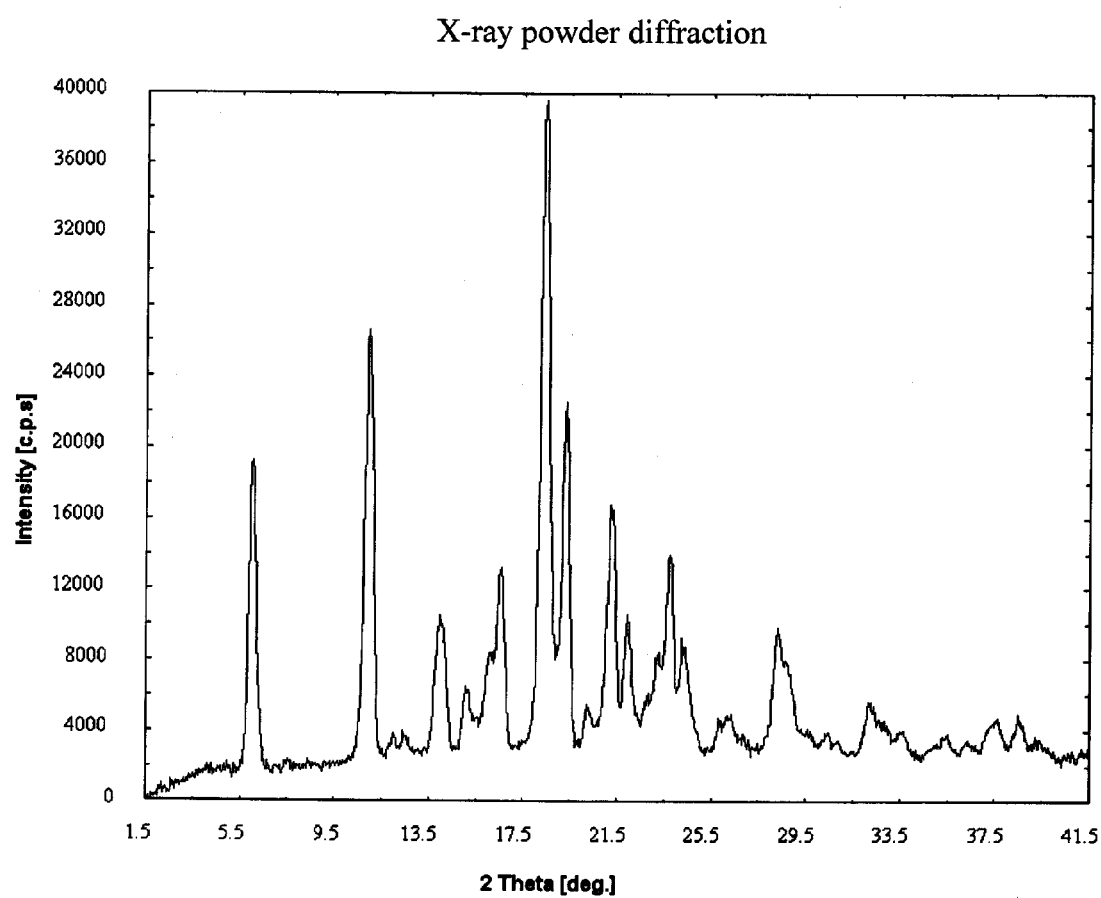
FIG. 15 sets forth identifying data for another group of isomorphic solvates of the compound of Formula I, above, including 1,4-dioxane solvate whose X-ray powder diffraction pattern is shown in FIG. 15A.
Figure 15B:
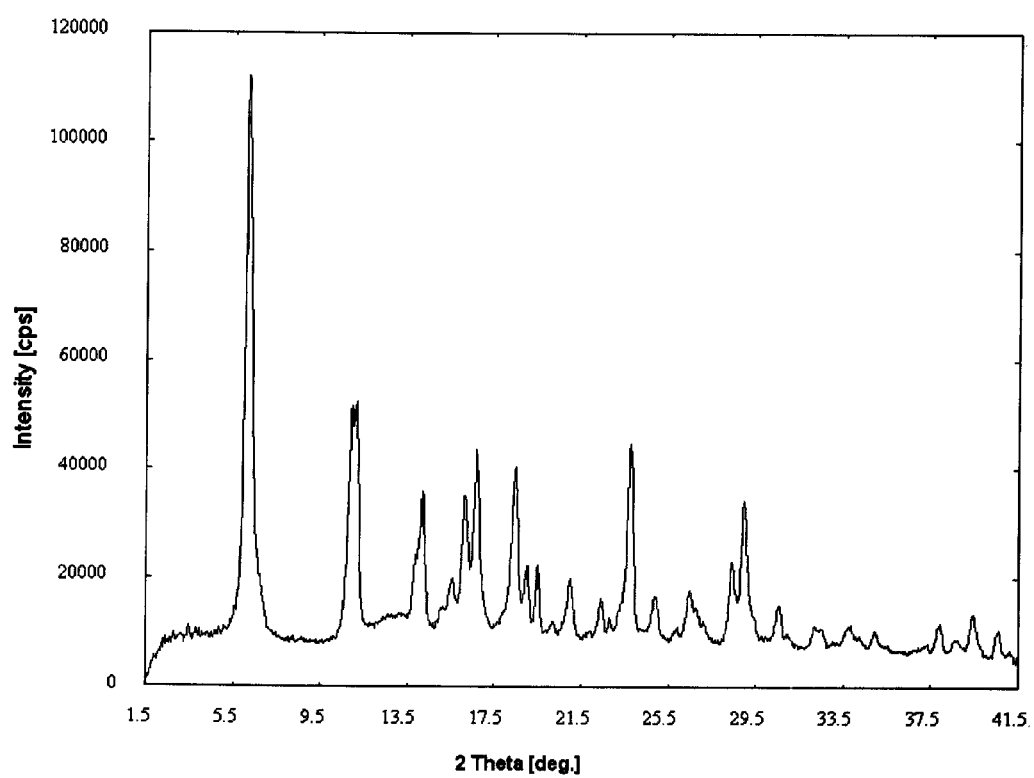
Figure 15C:
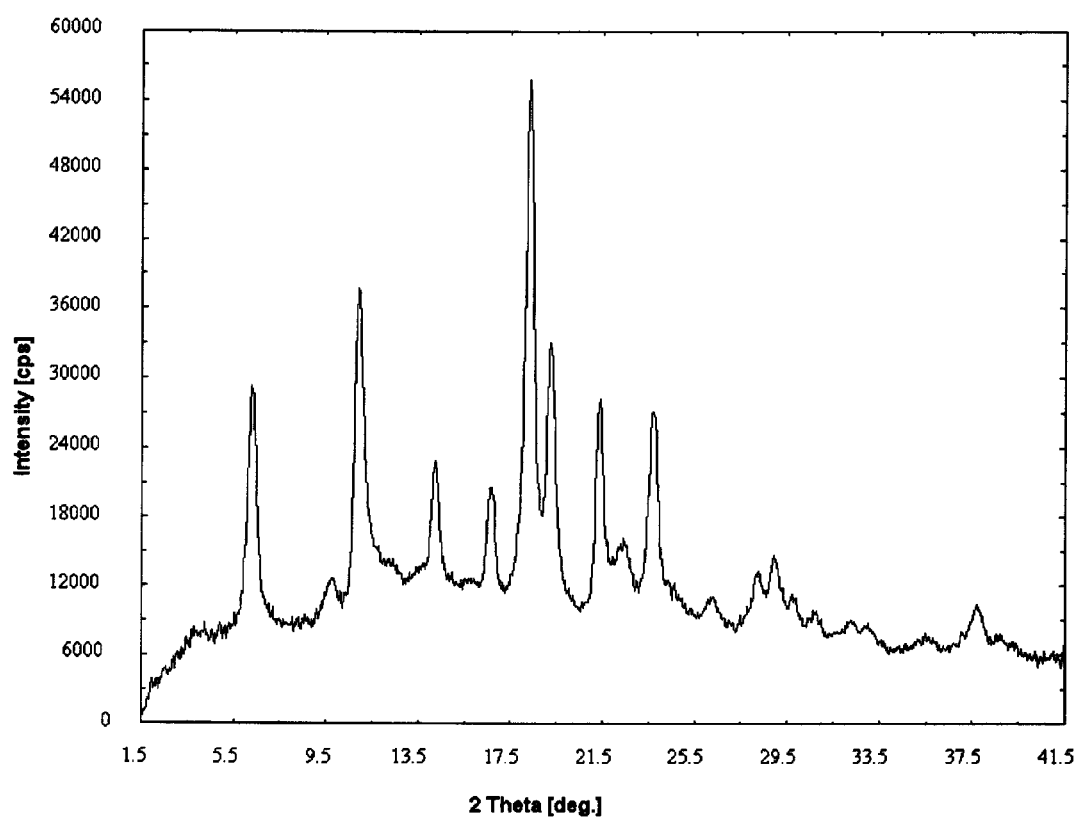
Figure 15E:
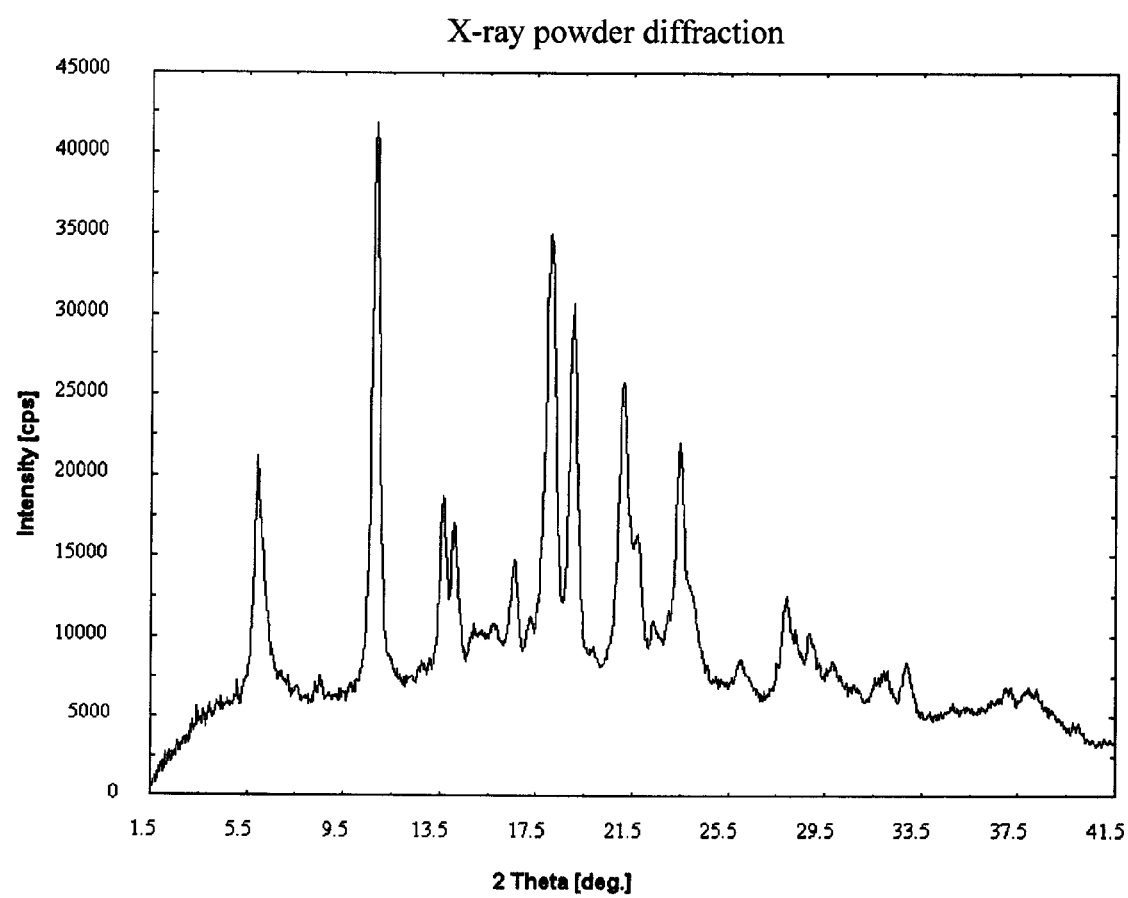
Figure 15F:
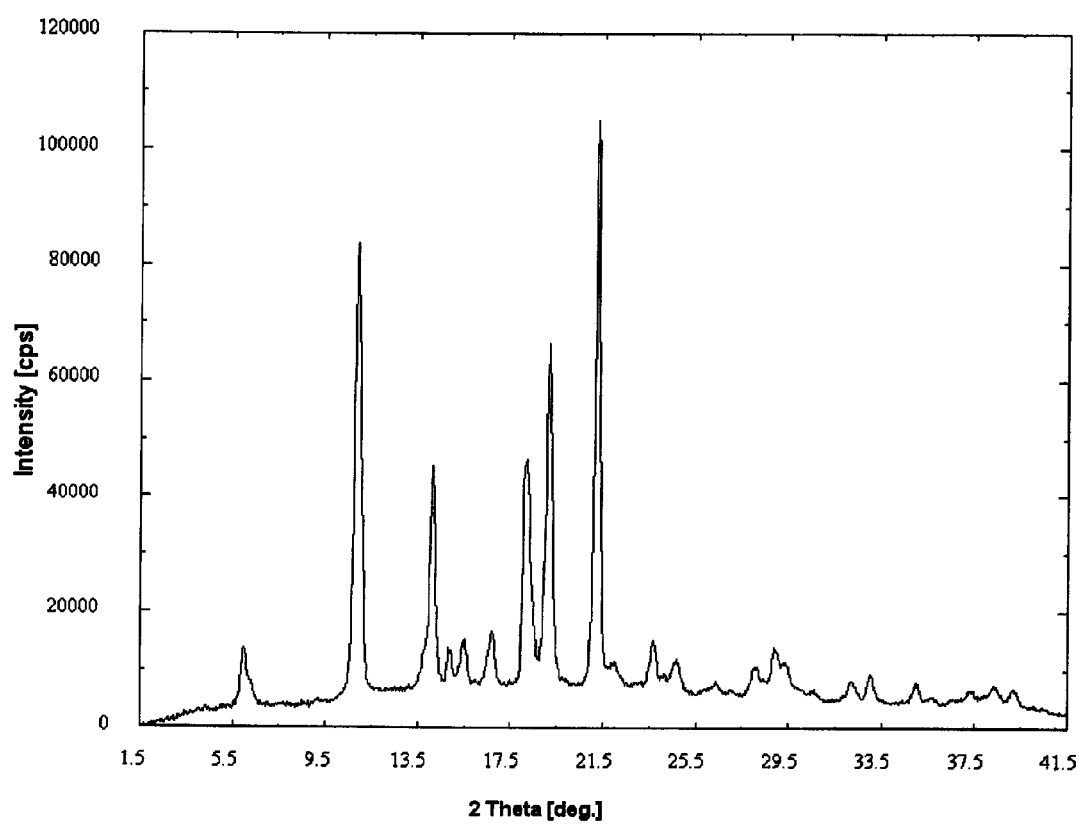
Figure 15G:
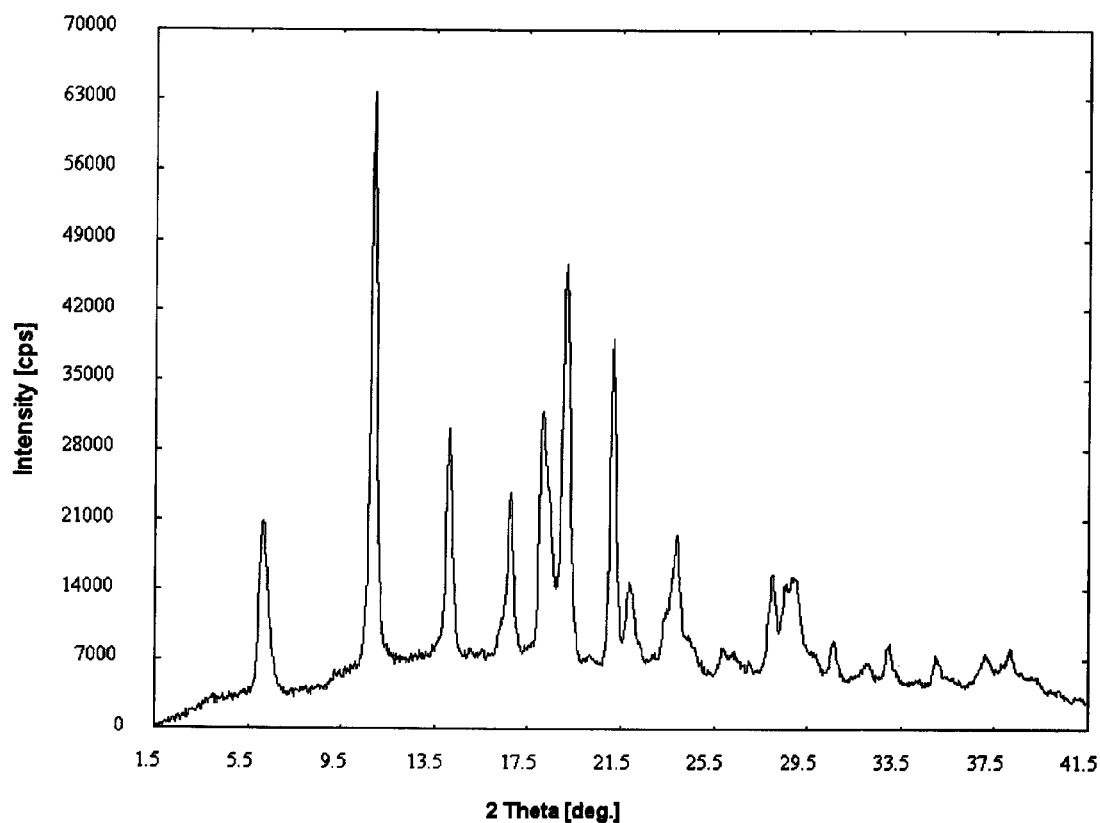
Figure 15I:
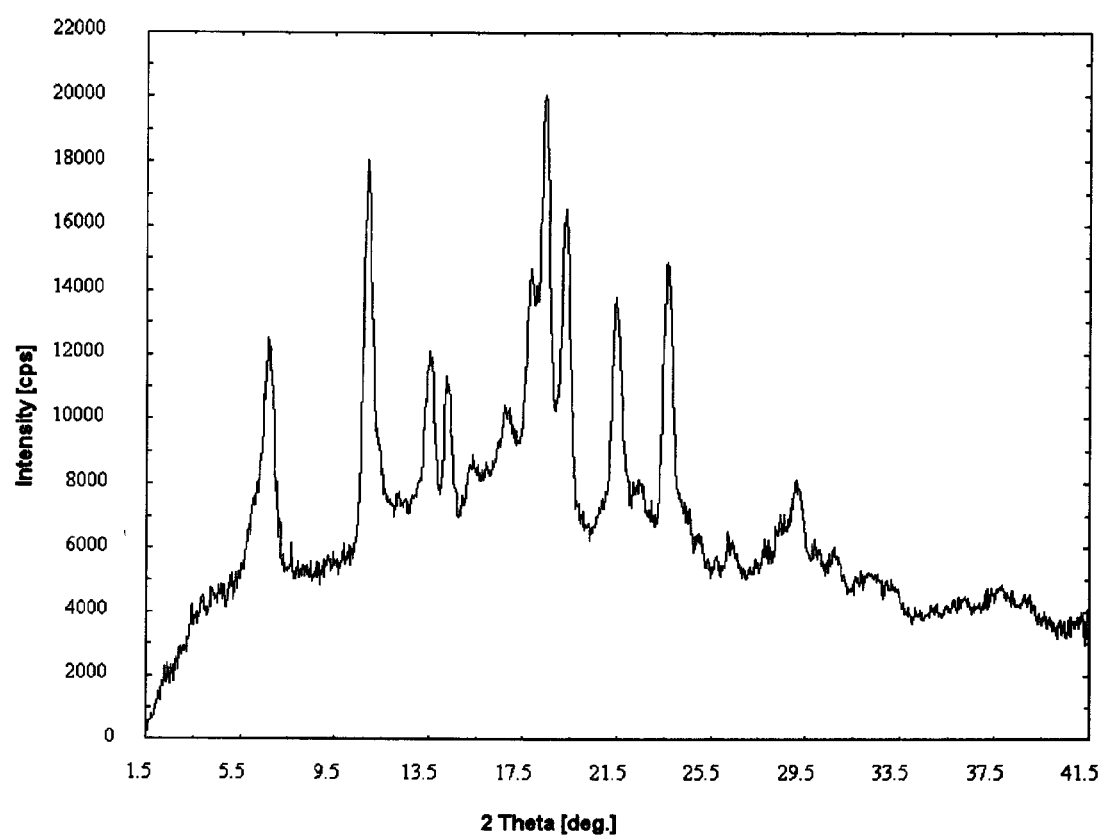
Figure 15J:
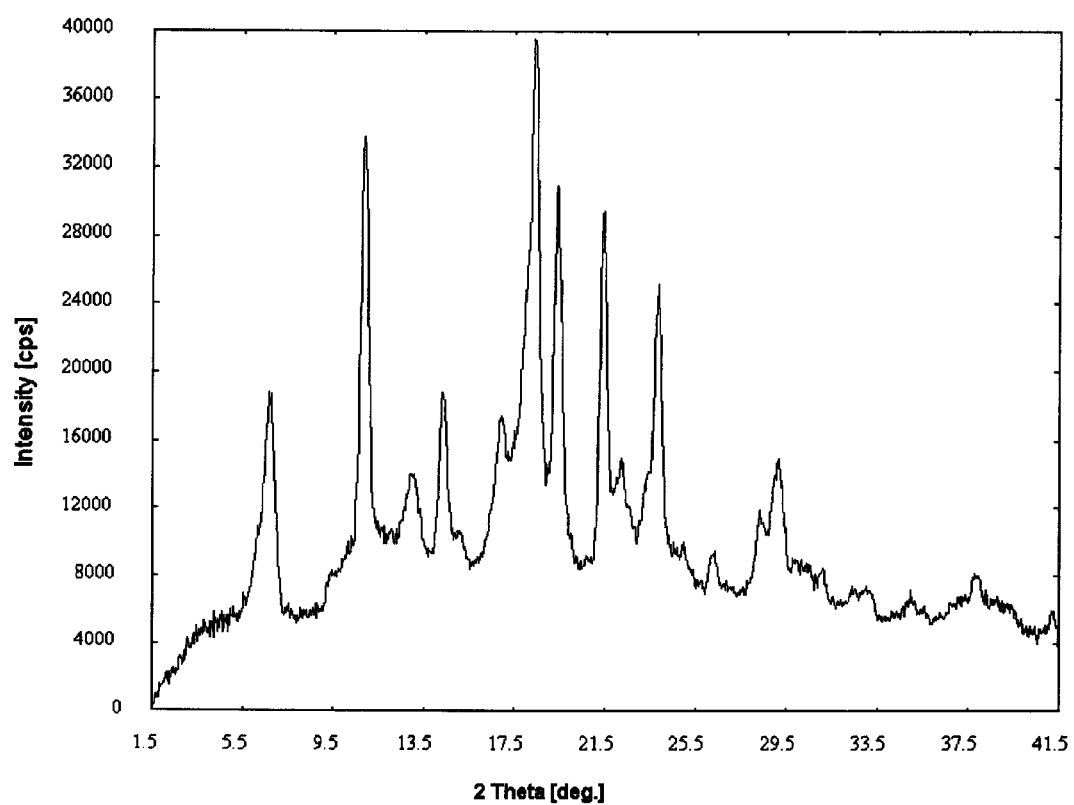
Figure 15K:
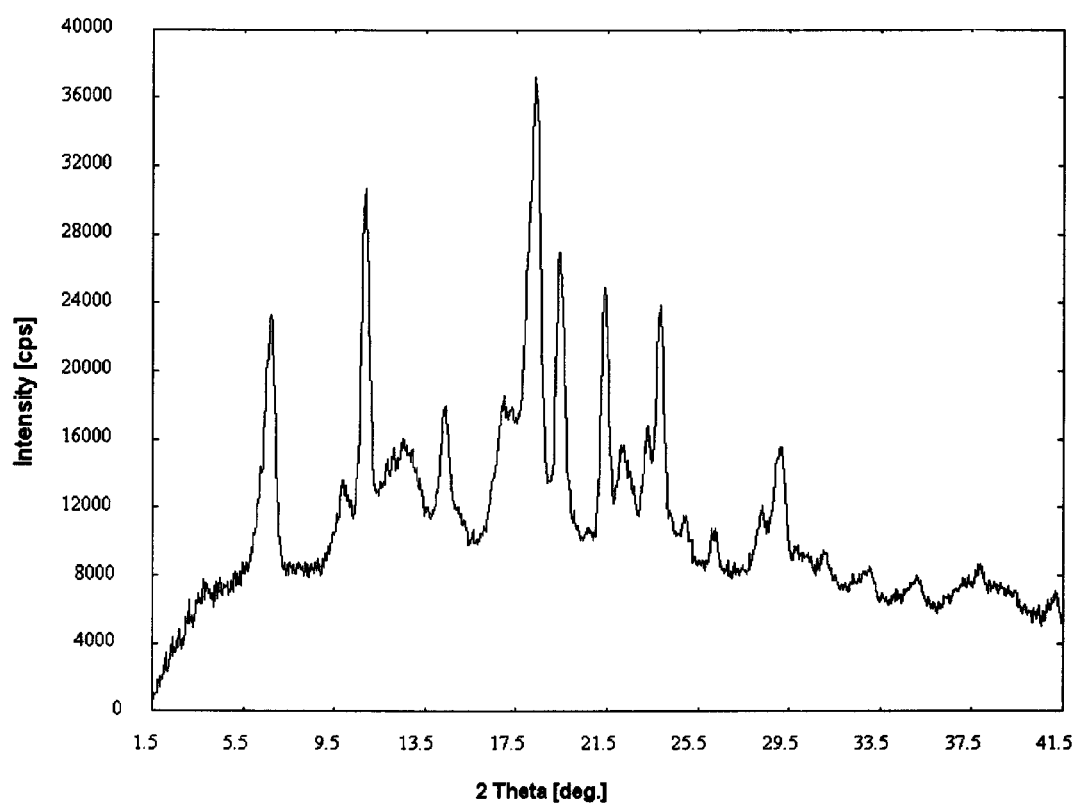
Figure 15L:
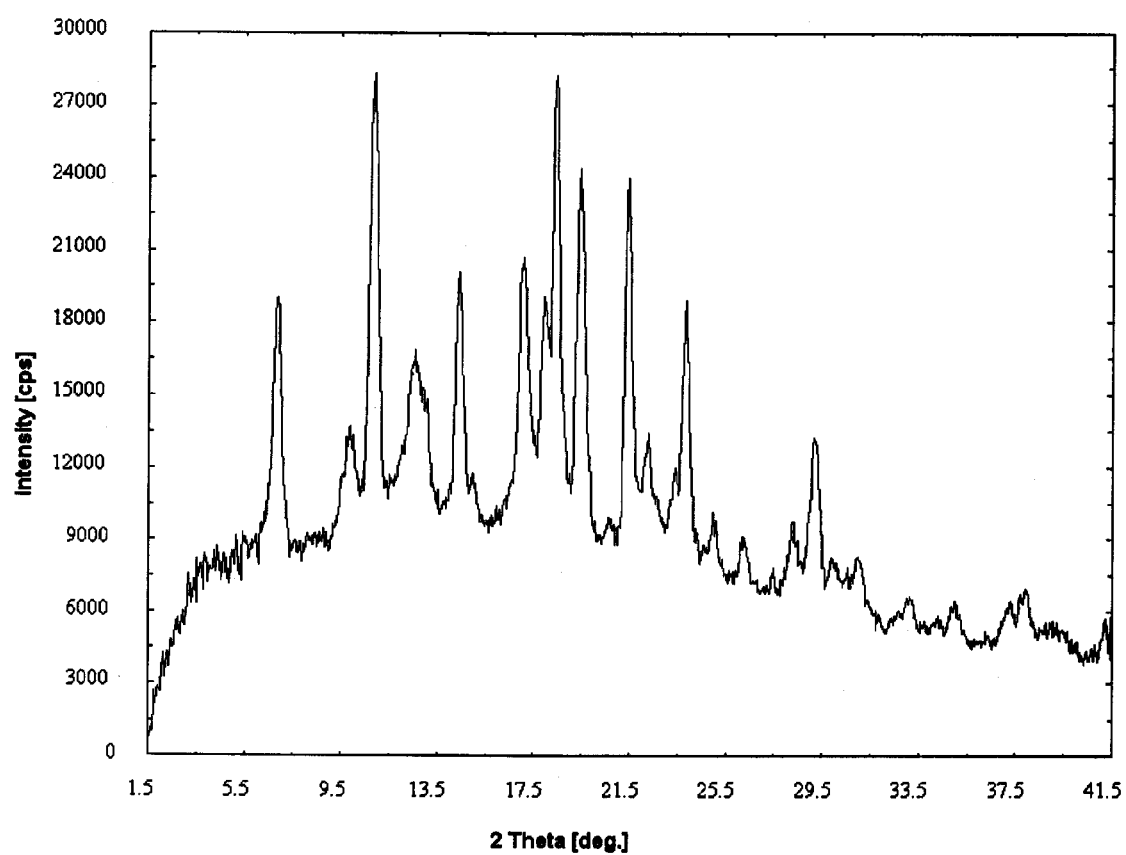
Figure 15M:
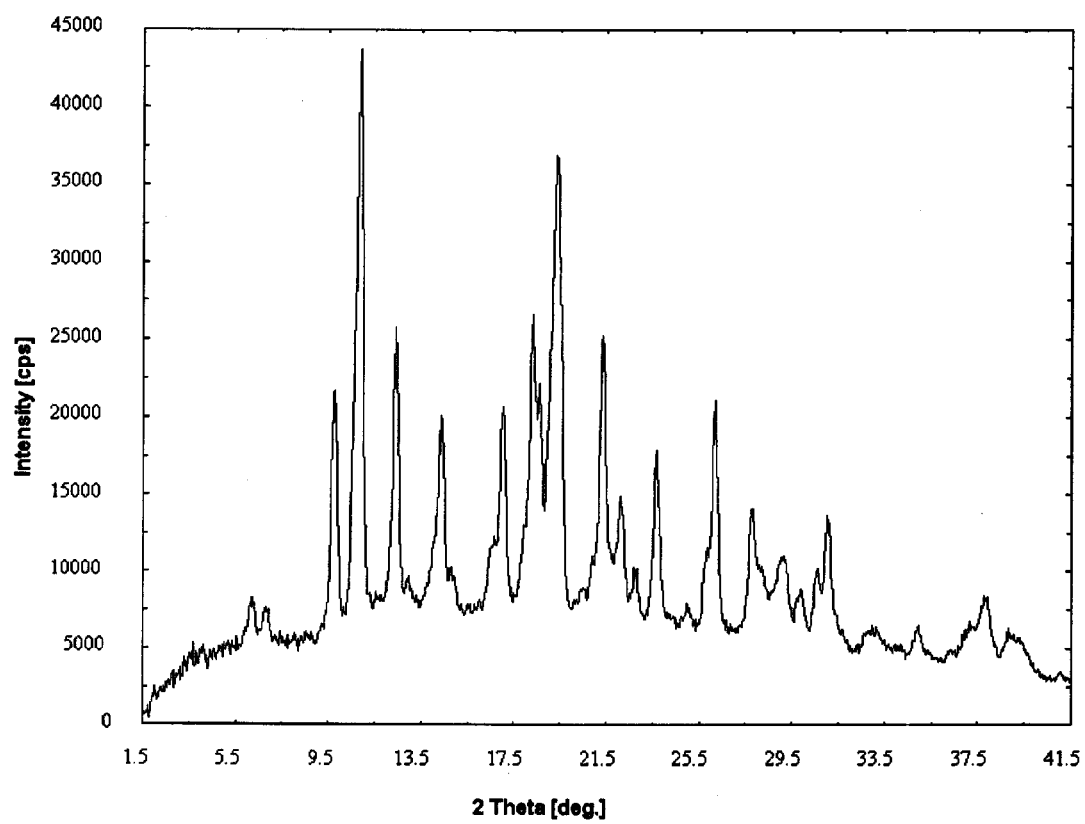

tetrahydrofuran (THF) solvate whose X-ray powder diffraction pattern is shown in FIG. 15B;

mixed ethyl acetate/n-heptane solvate whose X-ray powder diffraction pattern is shown in FIG. 15C;

ethyl acetate solvate whose X-ray powder diffraction pattern is shown in FIG. 15D1 (calculated XRPD pattern) and FIG. 15D2 (experimental XRPD pattern);

n-propyl acetate solvate whose X-ray powder diffraction pattern is shown in FIG. 15E;

mixed ethyl acetate/cyclohexane solvate whose X-ray powder diffraction pattern is shown in FIG. 15F;

mixed ethyl acetate/toluene solvate whose X-ray powder diffraction pattern is shown in FIG. 15G;

isopropyl acetate solvate whose X-ray powder diffraction pattern is shown in FIG. 15H1 (calculated XRPD pattern) and FIG. 15H2 (experimental XRPD pattern);

n-propyl acetate solvate whose X-ray powder diffraction pattern is shown in FIG. 15I;

mixed 1,4-dioxane/n-heptane solvate whose X-ray powder diffraction pattern is shown FIG. 15J;

mixed 1,4-dioxane/toluene solvate whose X-ray powder diffraction pattern is shown FIG. 15K;

mixed 1,2-dimethoxyethane/toluene solvate whose X-ray powder diffraction pattern is shown in FIG. 15L; and methylbutyrate solvate whose X-ray powder diffraction pattern is shown in FIG. 15M.

DETAILED DESCRIPTION OF THE INVENTION

"Polymorph", as generally understood, refers to a solid phase of a compound which occurs in several distinct forms due to different arrangements and/or confirmations of its molecular crystal lattice. As used herein, the term "polymorph" includes solid phases resulting from packing polymorphism and conformational polymorphism, and therefore may include different unsolvated crystal forms of a compound, and may include the crystalline forms made by removing the solvent from a solvate.

In particular embodiments of the present invention, pure, single polymorphs as well as mixtures comprising two or more different polymorphs are contemplated, e.g., a mixed hydrate-solvate or mixed solvate-solvate. A pure, single polymorph may be substantially free from other polymorphs. "Substantially free", as used herein, signifies that other polymorph(s) are present in an amount less than about 20 weight percent, more preferably less than about 10 weight percent and most preferably less than about 5 weight percent.

Additional technical terms used to describe the present invention, and their meanings, are provided below.

Crystalline phase (material): is a solid substance in which the atoms, molecules or ions are arranged in an orderly repeated pattern extending in all three spatial dimensions (called crystal lattice).

Amorphous phase (material): is a solid or semi-solid substance that unlike the crystalline phase has no long range order of molecular packing or well-defined molecular conformation if the molecules are conformationally flexible.

Form: is a crystalline phase of a substance with or without solvent and/or water of crystallization contained in the crystal lattice that possesses distinct arrangements and/or conformations of the molecules in the crystal lattice detectable by XRPD and single crystal X-ray crystallography among other techniques (i.e., spectroscopic techniques). The solvent and/or water may be present in a stoichiometric and/or non-stoichiometric amount in the crystal lattice.

Forms with cavities: forms that contain cavities, channels or void spaces (all of which are referred to here as cavities) in the crystal lattice. These forms may contain solvents and/or water in stoichiometric or non-stoichiometric amounts in the cavities.

Anhydrate (polymorph): a form with no solvent and/or water of crystallization in the crystal lattice; residual surface solvent and/or water not making part of the crystal lattice might be present.

Anhydrous (polymorph): a form with no solvent and/or water of crystallization in the crystal lattice and also no residual surface solvent and/or water.

Solvate: a form that contains molecules of the solvent of crystallization in a stoichiometric and/or non-stoichiometric amount in the crystal lattice. A stoichiometric solvate contains a discrete amount of solvent relative to the compound molecule in the crystal structure. A non-stoichiometric solvate contains in the crystal lattice a non-discrete or continuous change in the solvent stoichiometry relative to the compound molecules.

Hydrate: solvate in which the solvent of crystallization contained in the crystal lattice is water. Similar to solvates, hydrates can be stoichiometric or non-stoichiometric.

Mixed hydrate/solvate: solvate in which the solvents of crystallization contained in the crystal lattice are both solvent and water. Mixed hydrates/solvates can be stoichiometric and/or non-stoichiometric.

Isomorphic solvates: are solvates that possess similar crystal structure properties (same symmetries and similar unit cell parameters and crystal packing) while having different chemical compositions (i.e., different solvent and/or water molecules incorporated in the crystal lattice). The unit cell parameters of the isomorphic solvates within a class can differ as a function of the size of the incorporated solvent. The solvent molecules of an isomorphic solvate can be hydrogen bonded to the parent molecule and/or contained in the cavities of the crystal structure (also called a void space or channel).

Molecular ratio: the molecular ratio in a solvate of solvent molecules relative to the compound molecules in the crystal structure. Depending on the solvate, the molecular ratio of in the crystal structure may be either a stoichiometric ratio or a non-stoichiometric ratio.

The X-ray powder diffraction pattern of crystalline Form VIII and the various hydrates and solvates of the present invention can be determined using conventional techniques and equipment known to those skilled in the art of physical characterization. The diffraction patterns of FIGS. 1-15 were obtained using a high-throughput X-ray powder diffraction set-up. The well-plates were mounted on a Bruker GADDS diffractometer equipped with a Hi-Star area detector. The data collection was carried out at room temperature using monochromatic CuKα radiation in the region of 2θ between 1.5° and 41.5°. The diffraction pattern of each well was collected with an exposure time of 1-3 minutes.

A powder sample of each of Form VIII and the various novel hydrates and solvates exemplified below was used to produce the X-ray powder diffraction patterns of FIGS. 1-15, respectively. The X-ray diffraction patterns for each of Form VIII and the novel hydrates and solvates are unique to the particular form. Anhydrate Form VIII and each of the novel hydrates and solvates exhibit a diffraction pattern with a unique set of diffraction peaks which can be expressed in 2 theta angles)(°), d-spacings (Å) and/or relative peak intensities.

2 Theta diffraction angles and corresponding d-spacing values account for positions of various peaks in the X-ray powder diffraction pattern. D-spacing values are calculated with observed 2 theta angles and copper K.alpha.1 wavelength using the Bragg equation. Slight variations in observed 2 theta angles and d-spacings are expected based on the specific diffractometer employed and the analyst's sample preparation technique. Greater variation is expected for the relative peak intensities. Identification of the exact crystal form of a compound should be based primarily on observed 2 theta angles or d-spacings with lesser importance placed on relative peak intensities. In a mixture of crystal forms, the strongest diffraction peak for each form may overlap with the diffraction peak of another form. In a mixture of crystal forms, identification may be based on the presence of a lesser intensity peak that does not overlap with the other crystal forms.

Each of the anhydrate crystalline Form VIII, hydrates and/or solvates of 5,6-Dichloro-2-(isopropylamino)-1-(β-L-ribofuranosyl)-1H-benzimidazole described herein can also be identified by the presence of multiple characteristic 2 theta angle peaks including two, three, four, five, six, seven, eight, nine, or ten of the 2 theta angles which are reasonably characteristic of the particular crystalline form.

Some margin of error may be present in each of the 2 theta angle assignments and d-spacings reported herein. The error in determining d-spacings decreases with increasing diffraction scan angle or decreasing d-spacing. The margin of error in the 2 theta angles reported in the following examples for Form VIII and the various hydrates and solvates is approximately 0.04 degrees for each peak assignment. The margin of error in d-spacing values for Form VII and the solvates is approximately 0.01 Angstroms.

Since some margin of error is possible in the assignment of 2 theta angles and d-spacings, the preferred method of comparing X-ray powder diffraction patterns in order to identify a particular crystalline form is to overlay the X-ray powder diffraction pattern of the newly discovered form over the X-ray powder diffraction pattern of a known form. For example, one skilled in the art can overlay on FIG. 1 an X-ray powder diffraction pattern of an unidentified crystalline form of 5,6-dichloro-2-(isopropylamino)-1-(β-L-ribofuranosyl)-1H-benzimidazole, obtained using the methods described herein, and readily determine whether the X-ray diffraction pattern of the unidentified form is substantially the same as the X-ray powder diffraction pattern of Form VIII. If the X-ray powder diffraction pattern is substantially the same as FIG. 1, the previously unknown crystalline form can be readily and accurately identified as Form VIII. The same technique can be used to determine if an unidentified crystalline form is any of the hydrate or solvate forms of 5,6-dichloro-2-(isopropylamino)-1-(β-L-ribofuranosyl)-1H-benzimidazole described herein by overlaying the X-ray powder diffraction pattern over FIGS. 2-15, respectively.

Although 2 theta angles or d-spacings are the primary method of identifying a particular crystalline form, it may be desirable to also compare relative peak intensities. As noted above, relative peak intensities may vary depending upon the specific diffractometer employed and the analyst's sample preparation technique. The peak intensities are reported as intensities relative to the peak intensity of the strongest peak. The intensity units on the X-ray diffraction plot are counts/sec. The absolute counts=counts/time×count time=counts/sec×10 sec.

Other methods of physical characterization can also be employed to identify the anhydrate crystalline Form VIII, hydrates or solvates of the present invention. For example, melting point, differential scanning calorimetry, infrared spectra, and moisture sorption are all techniques known to those skilled in the art to be useful for the physical characterization of a crystalline form, hydrate or solvate. These techniques may be employed alone or in combination to characterize a given anhydrate crystalline form, hydrate or solvate.

The invention relates to the anhydrate crystalline Form VIII, hydrates and solvates both in pure form and in admixture with other anhydrate forms, hydrates or solvates of the compound of formula (I). By way of example, the n-propyl acetate solvate from class 2 isomorphic solvates, described in Example 15, below, partially desolvated and transformed to the anhydrate Form VI after storage in the well-plate under ambient temperature and relative humidity for approximately 3 weeks. In a similar manner, the t-butylmethyl ether solvate 2, described in Example 9, below, partially transformed into Form VI after approximately 4 weeks of storage under ambient conditions. Another example is the less stable acetonitrile solvate, described in Example 8, below, that completely desolvated and transformed to the anhydrate Form V under the same storage conditions after approximately 3 weeks.

The present invention also expressly contemplates mixtures of any of the foregoing anhydrate crystalline form, hydrates or solvates with one or more of the amorphous compound of formula (I), and/or other anhydrous crystalline forms and solvates previously described. It should be understood that admixtures of a particular crystalline form, hydrate or solvate with amorphous compound of formula (I) and/or other crystalline forms, hydrates or solvates may result in the masking or absence of one or more of the foregoing X-ray powder diffraction peaks described above for that particular form. Methods are known in the art for analyzing such admixtures of crystalline forms in order to provide for the accurate identification of the presence or absence of particular crystalline forms in the admixture.

In addition to the foregoing, any of the anhydrate crystalline forms or solvates of the present invention may be in admixture with novel or known hydrated crystalline forms. For example in any batch containing the anhydrate crystalline Form VIII of formula (I), there may also be hydrated crystalline forms of the compound.

As previously mentioned, crystalline Form VIII and the hydrate and solvate forms of the compound of formula (I) described herein are useful in medical therapy, e.g. in the treatment or prophylaxis of a viral disease in a patient in need thereof, e.g. a mammal such as a human. The compound of formula (I) in anhydrate crystalline Form VIII and the hydrates and solvates of such compound described herein are especially useful for the treatment or prophylaxis of viral diseases such as herpes virus infections, for example, CMV infections, as well as disease caused by hepatitis B and hepatitis C viruses. In addition to its use in human medical therapy, the compound of formula (I) anhydrous crystalline forms and solvates can be administered to other patients for treatment or prophylaxis of viral diseases, e.g. to other mammals.

As used herein, the term prophylaxis includes the prevention of infection, the prevention of occurrence of symptoms and the prevention of recurrence of symptoms.

Appropriate amounts of the polymorphs described herein for administration in the treatment or prophylaxis of herpes viral infection are essentially the same as described in U.S. Pat. Nos. 6,469,160 and 6,482,939, which also describe suitable dose forms and routes of administration.

The novel crystalline form and solvates of the invention can be administered conveniently in powder, tablet, capsule or suspension form.

The following examples describe the invention in further detail. These examples are provided for illustrative purposes only, and should in no way considered as limiting the invention.

The results of the characterizations of the new forms of the compound of formula (I) are set forth in Table 1.

Example 1

Form VIII

A saturated solution of compound of formula (I), Form VI, in propionitrile was made at room temperature by adding 1 mL of propionitrile to approximately 500 mg of Form VI. The saturated solution was stirred for approximately 1 h and subsequently filtered through a filter of 0.45 μm pore size. A reverse addition of 200 μL of the as prepared saturated solution was added at once to 800 μL of toluene acting as anti-solvent. After precipitation the solid material was separated from solution and dried under vacuum (200 mbar) at room temperature for approximately 25 h. The resulting solid material was analyzed as described in Table 1.

The characteristic XRPD peaks of Form VIII are as follows:

| 2-theta (°) | Relative intensity (%) |
| --- | --- |
| 8.42 | 15 |
| 10.94 | 100 |
| 17.00 | 60 |
| 18.78 | 23 |
| 21.79 | 19 |
| 22.27 | 22 |
| 29.14 | 26 |
| 33.03 | 15 |

Example 2

Dihydrate

Approximately 397 mg of compound of formula (I), Form VI, was dispensed in 1 mL solvent mixture of 1-propanol and water (50/50 v/v) at room temperature. The resulting slurry was heated at 40° C. and kept at this temperature for approximate 160 min after which the slurry was filtered at the respective temperature through a filter of 0.45 μm pore size. The resulted solution after filtration was kept for 30 minutes at 40° C. then cooled with a cooling rate of 20° C./h until reaching a temperature of 5° C. The solution was aged at this temperature for approx. 8 days. The solvent mixture was then evaporated under vacuum at room temperature, in two steps: approximately 98 h at 200 mbar followed by approximately 44 h at 5 mbar. The solid product of the di-hydrate crystallized on the side walls of the experimental vial while oily-like product was obtained in the bottom of the vial. The resulting solid material was analyzed as described in Table 1.

The characteristic XRPD peaks of this dihydrate are as follows:

| 2-theta (°) | Relative intensity (%) |
| --- | --- |
| 4.70 | 25 |
| 7.26 | 100 |
| 10.98 | 17 |
| 12.67 | 20 |
| 13.93 | 17 |
| 15.12 | 17 |
| 16.17 | 19 |
| 17.19 | 23 |
| 18.91 | 16 |
| 21.94 | 17 |
| 26.17 | 22 |
| 27.02 | 17 |
| 27.89 | 21 |
| 28.70 | 17 |

Example 3

Monohydrate

Approximately 379 mg of compound of formula (I), Form VI, was dispensed in 1 mL solvent mixture of 1,2-dimethoxyethane and water (50/50 v/v) at room temperature. The resulting slurry was heated at 40° C. and kept at this temperature for approximate 160 min after which the slurry was filtered at the respective temperature through a filter of 0.45 μm pore size.

The resulted solution after filtration was kept for 30 minutes at 40° C. then cooled with a cooling rate of 20° C./h until reaching a temperature of 5° C. The solution was aged at this temperature for approx. 8 days. The solvent mixture was then evaporated under vacuum at room temperature, in two steps: approximately 98 h at 200 mbar followed by approximately 44 h at 5 mbar. The solid product of the mono-hydrate crystallized on the side walls of the experimental vial while oily-like product was obtained in the bottom of the vial. The resulting solid material was analyzed as described in Table 1.

The characteristic XRPD peaks of this monohydrate are as follows:

| 2-theta (°) | Relative intensity (%) |
|---|---|
| 6.12 | 77 |
| 7.61 | 100 |
| 9.61 | 79 |
| 11.00 | 56 |
| 14.44 | 54 |
| 16.87 | 81 |
| 18.40 | 53 |
| 19.50 | 44 |
| 21.17 | 52 |
| 21.93 | 58 |
| 25.75 | 46 |
| 26.37 | 54 |
| 27.94 | 43 |
| 28.37 | 42 |
| 29.71 | 37 |

Example 4

Hydrate/Methanol Solvate #1

Approximately 80 mg of compound of formula (I), Form VI, was dispensed in 2504 of methanol at room temperature. The resulting slurry was placed at 5° C. and kept under stirring to this temperature for approximately 120 h. The solid material was then separated from solution at room temperature and analyzed as described in Table 1. No drying under vacuum was applied prior to the analyses.

The characteristic XRPD peaks of this hydrate/methanol solvate #1 are as follows:

| 2-theta (°) | Relative intensity (%) |
|---|---|
| 7.30 | 100 |
| 9.02 | 19 |
| 11.50 | 14 |
| 14.01 | 16 |
| 17.81 | 19 |
| 21.17 | 26 |
| 23.18 | 22 |
| 25.75 | 20 |
| 27.51 | 18 |
| 29.53 | 12 |

Example 5

Hydrate/Ethyl Formate Solvate

Approximately 122 mg of compound of formula (I), Form VI, was dissolved in 1.3 mL ethyl formate. The solution was stirred for 3 h at room temperature then filtered through a filter of 0.45 μm pore size. A quantity of 200 μL of filtered solution was then exposed (at room temperature) to water vapors for approximately 14 days. The solid material was collected after 14 days of exposure and analyzed, as detailed in Table 1.

The characteristic XRPD peaks of this hydrate/ethyl formate solvate are as follows:

| 2-theta (°) | Relative intensity (%) |
|---|---|
| 4.70 | 17 |
| 7.34 | 100 |
| 10.98 | 6 |
| 12.73 | 8 |
| 14.36 | 13 |
| 15.43 | 17 |
| 17.00 | 17 |
| 18.15 | 7 |
| 18.91 | 8 |
| 22.22 | 15 |
| 25.71 | 14 |
| 26.20 | 13 |

Example 6

Hydrate/Methanol Solvate #2

Approximately 123 mg of compound of formula (I), Form VI, was dispensed in 2504 solvent mixture of methanol and water (50/50 v/v) at room temperature. The resulting slurry was heated at 40° C. and kept at this temperature for approximate 160 min after which the resulting solution was filtered at the respective temperature through a filter of 0.45 μm pore size. The resulting solution after filtration was kept for 30 minutes at 40° C. then cooled with a cooling rate of 20° C./h until reaching a temperature of 5° C. The solution was kept at this temperature for approximately 8 days. The solvent mixture was then evaporated under vacuum at room temperature, in two steps: approximately 98 h at 200 mbar followed by approximately 44 h at 5 mbar. The resulting solid material was analyzed as described in Table 1.

The characteristic XRPD peaks of this hydrate/methanol solvate #2 are as follows:

| 2-theta (°) | Relative intensity (%) |
|---|---|
| 3.94 | 34 |
| 5.90 | 57 |
| 8.15 | 100 |
| 15.65 | 39 |
| 16.87 | 37 |
| 22.26 | 38 |
| 25.82 | 36 |

Example 7

T-Butylmethyl Ether Solvate 1

Approximately 125 mg solid of compound of formula (I), Form VI, was dispensed at room temperature in 250 μL tert-butyl methyl ether. The resulting slurry was kept at room temperature for approximately 30 h and then thermo-cycled five times between 25° C. and 60° C. The two indicated temperatures were reached by applying 10° C./h heating and cooling rates and the slurries were kept 30 minutes each time the 25° C. and 60° C. temperatures were reached. The solid material was then separated from solution at room temperature and analyzed as described in Table 1. No drying under vacuum was applied prior to the analyses.

The characteristic XRPD peaks of this t-butylmethyl ether solvate 1 are as follows:

| 2-theta (°) | Relative intensity (%) |
|---|---|
| 7.99 | 24 |
| 9.55 | 77 |
| 11.32 | 22 |
| 12.45 | 20 |
| 14.25 | 23 |
| 15.91 | 35 |
| 16.43 | 51 |
| 16.88 | 67 |
| 17.46 | 38 |
| 17.87 | 100 |
| 19.20 | 31 |
| 19.61 | 57 |
| 20.83 | 67 |
| 22.74 | 21 |
| 24.03 | 25 |
| 25.86 | 21 |
| 26.66 | 21 |
| 27.51 | 44 |
| 30.09 | 23 |

Example 8

Acetonitrile Solvate

Approximately 20 mg of compound of formula (I), Form VI, was dispensed in 200 μL methanol/water (80/20 v/v) solvent mixture. The resulting solution was freezed at −47° C. and dried at room temperature under vacuum (0.05 mbar) for 43 hours. The resulting solid material was then heated for approximately 2 h at 100° C. under vacuum (50 mbar). The dried solid material was then exposed at room temperature for 14 days to 2 mL acetonitrile vapors, then collected and analyzed as described in Table 1. No drying under vacuum was applied prior to the analyses.

The characteristic XRPD peaks of this acetonitrile solvate are as follows:

| 2-theta (°) | Relative intensity (%) |
|---|---|
| 7.95 | 41 |
| 9.11 | 29 |
| 10.54 | 100 |
| 13.13 | 90 |
| 14.42 | 37 |
| 18.30 | 52 |
| 20.62 | 32 |
| 21.31 | 34 |
| 22.17 | 55 |
| 26.37 | 45 |
| 26.99 | 53 |
| 27.71 | 56 |
| 30.90 | 46 |
| 32.71 | 22 |

Example 9

T-Butylmethyl Ether Solvate 2

Approximately 25 mg of compound of formula (I), Form VI, was dissolved at room temperature in 1 mL tert-butyl methyl ether. The resulting solution was stirred at room temperature for approximately 3 h. The solvent was then evaporated at room temperature under vacuum (200 mbar) for approximately 115 h. The solid material was then collected analyzed as described in Table 1.

The characteristic XRPD peaks of this t-butylmethyl ether solvate 2 are as follows:

| 2-theta (°) | Relative intensity (%) |
|---|---|
| 10.88 | 55 |
| 14.20 | 53 |
| 15.63 | 53 |
| 16.48 | 63 |
| 16.87 | 65 |
| 19.35 | 53 |
| 21.14 | 100 |
| 23.69 | 62 |
| 29.29 | 43 |

Example 10

N-Butyl Acetate Solvate

Approximately 75 mg of compound of formula (I), Form VI, was dispensed in 250₄ of n-butyl acetate, at room temperature. The resulting slurry was placed at 5° C. and kept under stirring to this temperature for approximately 120 h. The solid material was then separated from solution at room temperature and analyzed as described in Table 1. No drying under vacuum was applied prior to the analyses.

The characteristic XRPD peaks of this n-butyl acetate solvate are as follows:

| 2-theta (°) | Relative intensity (%) |
|---|---|
| 5.80 | 66 |
| 10.80 | 100 |
| 13.56 | 62 |
| 15.61 | 50 |
| 16.51 | 42 |
| 17.90 | 58 |
| 18.80 | 61 |
| 20.82 | 79 |
| 21.71 | 41 |
| 22.50 | 39 |
| 23.02 | 61 |
| 23.58 | 40 |
| 27.41 | 32 |
| 28.85 | 26 |

Example 11

Isopropyl Ether Solvate

Approximately 20 mg of compound of formula (I), Form VI, was dispensed in 250 μL of isopropyl ether, at room temperature. The resulting slurry was placed at 5° C. kept under stirring to this temperature for approximately 120 h. The solid material was then separated from solution at room temperature and analyzed as described in Table 1. No drying under vacuum was applied prior to the analyses.

The characteristic XRPD peaks of this isopropyl ether solvate are as follows:

| 2-theta (°) | Relative intensity (%) |
|---|---|
| 5.91 | 91 |
| 7.01 | 97 |
| 10.43 | 86 |
| 12.18 | 86 |
| 14.48 | 60 |
| 17.27 | 71 |
| 19.73 | 80 |
| 20.58 | 100 |

Example 12

1,2-Dimethoxyethane/Toluene Solvate

A saturated solution of compound of formula (I), Form VI in 1,2-dimethoxyethane was made at room temperature by adding 1.4 mL of 1,2-dimethoxyethane to approximately 698 mg of Form VI. The saturated solution was stirred for approximately 1 h and subsequently filtered through a filter of 0.45 μm pore size. A reverse addition of 200 μL of the as prepared saturated solution was added at once to 800 μL of toluene acting as anti-solvent. After precipitation the solid material was separated from solution and analyzed as described in Table 1. No drying under vacuum was applied prior to the analyses.

The characteristic XRPD peaks of this 1,2-dimethoxyethane/toluene solvate are as follows:

| 2-theta (°) | Relative intensity (%) |
|---|---|
| 6.05 | 47 |
| 6.41 | 34 |
| 10.82 | 100 |
| 13.65 | 43 |
| 14.05 | 69 |
| 16.39 | 38 |
| 16.82 | 52 |
| 18.22 | 99 |
| 18.70 | 94 |
| 21.01 | 66 |
| 21.74 | 64 |
| 23.53 | 52 |
| 23.99 | 70 |
| 26.25 | 21 |
| 27.68 | 24 |
| 28.33 | 31 |
| 28.84 | 49 |
| 30.46 | 23 |

Example 13

2,2-Dimethyl-3-Butanone Solvate

Approximately 509 mg of compound of formula (I), Form VI, was dispensed in 1 mL of 2,2,-dimethyl-3-butanone at room temperature. The resulting slurry was heated at 40° C. and kept at this temperature for approximate 160 min after which the slurry was filtered at the respective temperature through a filter of 0.45 μm pore size. The resulting solution after filtration was kept for 30 minutes at 40° C. then cooled with a cooling rate of 20° C./h until reaching a temperature of 5° C. The solution was kept at this temperature for approximately 8 days. The solvent was then evaporated under vacuum at room temperature, in two steps: approximately 98 h at 200 mbar followed by approximately 44 h at 50 mbar. The resulting solid material was analyzed as described in Table 1.

The characteristic XRPD peaks of this 2,2-dimethyl-3-butanone solvate are as follows:

| 2-theta (°) | Relative intensity (%) |
|---|---|
| 5.50 | 100 |
| 10.81 | 43 |
| 13.45 | 21 |
| 15.02 | 25 |
| 17.68 | 58 |
| 18.47 | 46 |
| 19.46 | 44 |
| 21.02 | 26 |
| 22.25 | 35 |
| 23.60 | 22 |
| 28.61 | 21 |

Example 14

Class 1 Isomorphic Solvates

14(a) Hexafluorobenzene Solvate

Approximately 24-30 mg of compound of formula (I), Form VI, was dispensed in an 5 mL stainless-steel vial containing 2 stainless-steel balls. A drop of 10 μL of hexafluorobenzene was subsequently added at room temperature and the closed vial was shaken for 30 minutes with a frequency of 30 oscillations/second. The resulting solid was analyzed as described in Table 1.

The characteristic XRPD peaks of this hexafluorobenzene solvate are as follow:

| 2-theta (°) | Relative intensity (%) |
|---|---|
| 7.26 | 66 |
| 9.09 | 60 |
| 10.86 | 100 |
| 21.21 | 53 |
| 14.45 | 52 |
| 15.46 | 62 |
| 16.58 | 50 |
| 17.89 | 49 |
| 18.65 | 43 |
| 21.18 | 55 |
| 25.74 | 52 |
| 26.66 | 48 |
| 27.57 | 39 |
| 28.77 | 42 |

14(b) Nitrobenzene Solvate:

Approximately 24-30 mg of compound of formula (I), Form VI, was dispensed in an 5 mL stainless-steel vial containing 2 stainless-steel balls. A drop of 10 μL of nitrobenzene was subsequently added at room temperature and the closed vial was shaken for 30 minutes with a frequency of 30 oscillations/second. The resulting solid was analyzed as described in Table 1.

The characteristic XRPD peaks of this nitrobenzene solvate are as follows:

| 2-theta (°) | Relative intensity (%) |
| --- | --- |
| 7.29 | 68 |
| 9.17 | 50 |
| 10.95 | 100 |
| 12.31 | 54 |
| 13.17 | 37 |
| 13.86 | 41 |
| 14.70 | 45 |
| 15.53 | 60 |
| 17.57 | 48 |
| 20.36 | 56 |
| 22.10 | 46 |
| 25.90 | 56 |
| 27.08 | 51 |
| 27.77 | 39 |
| 29.01 | 37 |

Various other aromatic organic solvents may be used to produce class 1 isomorphic solvates.

Table 2 sets forth the peak positions and relative peak intensity intervals for class 1 isomorphic solvates described in this example.

Example 15

Class 2 Isomorphic Solvates

15(a) 1,4-dioxane Solvate:

Approximately 126 mg of compound of formula (I), Form VI, was dispensed in 250 μL of 1,4-dioxane, at room temperature. The resulting slurry was placed at 5° C. and kept under stirring to this temperature for approximately 120 h. The solid material was then separated from solution at room temperature and analyzed as described in Table 1. No drying under vacuum was applied prior to the analyses.

The characteristic XRPD peaks of this 1,4-dioxane solvate are as follows:

| 2-theta (°) | Relative intensity (%) |
| --- | --- |
| 6.02 | 49 |
| 10.94 | 67 |
| 13.97 | 26 |
| 15.09 | 16 |
| 16.10 | 21 |
| 16.57 | 33 |
| 18.42 | 100 |
| 19.31 | 57 |
| 20.23 | 14 |
| 21.22 | 42 |
| 21.94 | 27 |
| 23.25 | 21 |
| 23.75 | 35 |
| 24.26 | 23 |
| 28.32 | 25 |

15(b) THF Solvate:

A saturated solution of compound of formula (I), Form VI in THF was made at room temperature by adding 1.4 mL of THF to approximately 700 mg of Form VI. The saturated solution was stirred for approximately 1 h and subsequently filtered through a filter of 0.45 μm pore size. A reverse addition of 200 μL of the as prepared saturated solution was added at once to 800 μL of toluene acting as anti-solvent. The solution was then aged for approx. 15 h at 5° C. After precipitation the solid material was separated from solution and dried under vacuum (200 mbar) at room temperature for approximately 25 h. The resulting solid material was analyzed as described in Table 1. See also Table 3.

The characteristic XRPD peaks of this THF solvate are as follows:

| 2-theta (°) | Relative intensity (%) |
| --- | --- |
| 6.15 | 100 |
| 10.93 | 46 |
| 18.45 | 36 |
| 19.49 | 20 |
| 21.00 | 18 |
| 23.74 | 40 |

* Due to the preferred orientation affecting the relative intensity (%), their values were not considered in Table 6 defining the general characteristic XRPD peaks relative intensities of the isomorphic class 2.

15(c) Ethyl Acetate/n-heptane Mixed Solvate:

A saturated solution of compound of formula (I), Form VI in ethyl acetate was made at room temperature by adding 1.5 mL of ethyl acetate to approximately 512 mg of Form VI. The saturated solution was stirred for approximately 1 h and subsequently filtered through a filter of 0.45 μm pore size. A reverse addition of 200 μL of the as prepared saturated solution was added at once to 800 μL of n-heptane acting as anti-solvent. After precipitation the solid material was separated from solution and dried under vacuum (200 mbar) at room temperature for approximately 25 h. The resulting solid material was analyzed as described in Table 1.

The characteristic XRPD peaks of this ethyl acetate/n-heptane mixed solvate are as follows:

| 2-theta (°) | Relative intensity (%) |
| --- | --- |
| 6.27 | 52 |
| 10.88 | 67 |
| 18.33 | 100 |
| 19.22 | 59 |
| 21.38 | 51 |
| 23.67 | 48 |

15(d) Ethyl Acetate Solvate:

Approximately 177 mg of compound of formula (I), Form VI, was dissolved in 1.1 mL ethyl acetate. The solution was stirred for 3 h at room temperature then filtered through a filter of 0.45 μm pore size. A quantity of 200 μL of filtered solution was then exposed (at room temperature) to cyclohexane vapors for approximately 14 days. The solid material was then stored at ambient conditions for approximate 3 weeks then collected and analyzed, as detailed in Table 1. See also Table 4.

The characteristic XRPD peaks of this ethyl acetate solvate are as follows:

| 2-theta (°) | Relative intensity (%) |
| --- | --- |
| 6.44 | 9 |
| 10.85 | 77 |
| 18.10 | 100 |

-continued

| 2-theta (°) | Relative intensity (%) |
|---|---|
| 19.10 | 97 |
| 21.26 | 46 |
| 23.67 | 18 |

* Due to the preferred orientation affecting the relative intensity (%), their values were not considered in Table 6 defining the general characteristic XRPD peaks relative intensities of the isomorphic class 2.

15(e) n-Propyl Acetate Solvate #1:

Approximately 57 mg of compound of formula (I), Form VI, was dispensed in 250 μL of n-propyl acetate, at room temperature. The resulting slurry kept under stirring at room temperature for approximately 120 h. The solid material was then separated from solution at room temperature, kept for approximate 4 weeks at ambient conditions then analyzed as described in Table 1. No drying under vacuum was applied prior to the analyses.

The characteristic XRPD peaks of this n-propyl acetate solvate #1 are as follows:

| 2-theta (°) | Relative intensity (%) |
|---|---|
| 5.94 | 50 |
| 10.82 | 100 |
| 18.08 | 83 |
| 19.01 | 73 |
| 21.09 | 65 |
| 23.45 | 52 |

15(f) Ethyl Acetate/Cyclohexane Mixed Solvate:

Approximately 177 mg of compound of formula (I), Form VI, was dissolved in 1.1 mL ethyl acetate. The solution was stirred for 3 h at room temperature then filtered through a filter of 0.45 μm pore size. A quantity of 200 μL of filtered solution was then exposed (at room temperature) to cyclohexane vapors for approximately 14 days. The solid material was then collected and analyzed, as detailed in Table 1.

The characteristic XRPD peaks of this ethyl acetate/cyclohexane mixed solvate are as follows:

| 2-theta (°) | Relative intensity (%) |
|---|---|
| 5.97 | 12 |
| 10.85 | 75 |
| 18.18 | 42 |
| 19.14 | 60 |
| 21.22 | 100 |
| 23.65 | 14 |

* Due to the preferred orientation affecting the relative intensity (%), their values were not considered in Table 6 defining the general characteristic XRPD peaks relative intensities of the isomorphic class 2.

15(g) Ethyl Acetate/Toluene Mixed Solvate:

Approximately 177 mg of compound of formula (I), Form VI, was dissolved in 1.1 mL ethyl acetate. The solution was stirred for 3 h at room temperature then filtered through a filter of 0.45 μm pore size. A quantity of 200 μL of filtered solution was then exposed (at room temperature) to toluene vapors for approximately 14 days. The solid material was then collected and analyzed, as detailed in Table 1.

The characteristic XRPD peaks of this ethyl acetate/toluene mixed solvate are as follows:

| 2-theta (°) | Relative intensity (%) |
|---|---|
| 6.12 | 33 |
| 10.86 | 100 |
| 18.14 | 50 |
| 19.15 | 73 |
| 21.13 | 62 |
| 23.94 | 29 |

* Due to the preferred orientation affecting the relative intensity (%), their values were not considered in Table 6 defining the general characteristic XRPD peaks relative intensities of the isomorphic class 2.

15(h) Isopropyl Acetate Solvate:

Approximately 240 mg of compound of formula (I), Form VI, was dissolved in 1.1 mL isopropyl acetate. The solution was stirred for 3 h at room temperature then filtered through a filter of 0.45 μm pore size. A quantity of 200 μL of filtered solution was then exposed (at room temperature) to n-heptane vapors for approximately 14 days. The solid material was then collected and analyzed, as detailed in Table 1. See also Table 5.

The characteristic XRPD peaks of this isopropyl acetate solvate are as follows:

| 2-theta (°) | Relative intensity (%) |
|---|---|
| 6.09 | 12 |
| 10.86 | 100 |
| 18.18 | 42 |
| 19.18 | 91 |
| 21.22 | 82 |
| 23.73 | 18 |

* Due to the preferred orientation affecting the relative intensity (%), their values were not considered in Table 6 defining the general characteristic XRPD peaks relative intensities of the isomorphic class 2.

15(i) N-Propyl Acetate Solvate #2:

Approximately 57 mg of compound of formula (I), Form VI, was dispensed in 250 μL of n-propyl acetate, at room temperature. The resulting slurry kept under stirring at room temperature for approximately 120 h. The solid material was then separated from solution at room temperature and analyzed as described in Table 1. No drying under vacuum was applied prior to the analyses.

The characteristic XRPD peaks of this n-Propyl acetate solvate #2 are as follows:

| 2-theta (°) | Relative intensity (%) |
|---|---|
| 6.67 | 62 |
| 10.89 | 90 |
| 18.42 | 100 |
| 19.30 | 83 |
| 21.41 | 68 |
| 23.62 | 74 |

15(j) 1,4-Dioxane/n-Heptane Mixed Solvate:

A saturated solution of compound of formula (I), Form VI in 1,4-dioxane was made at room temperature by adding 1.4 mL of 1,4-dioxane to approximately 717 mg of Form VI. The saturated solution was stirred for approximately 1 h and subsequently filtered through a filter of 0.45 μm pore size. A reverse addition of 200 μL of the as prepared saturated solution was added at once to 800 μL of n-heptane acting as anti-solvent. After precipitation the solid material was separated from solution and dried under vacuum (200 mbar) at room temperature for approximately 25 h. The resulting solid material was analyzed as described in Table 1.

The characteristic XRPD peaks of this 1,4-dioxane/n-heptane mixed solvate are as follows:

| 2-theta (°) | Relative intensity (%) |
|---|---|
| 6.65 | 48 |
| 10.83 | 85 |
| 18.36 | 100 |
| 19.37 | 78 |
| 21.41 | 74 |
| 23.82 | 64 |

(15k) 1,4-Dioxane/Toluene Mixed Solvate:

A saturated solution of compound of formula (I), Form VI in 1,4-dioxane was made at room temperature by adding 1.4 mL of 1,4-dioxane to approximately 717 mg of Form VI. The saturated solution was stirred for approximately 1 h and subsequently filtered through a filter of 0.45 μm pore size. A forward addition of 2004 of toluene acting as anti-solvent was added to 200 μL of as prepared saturated 1,4-dioxane solution. After precipitation the solid material was separated from solution and dried under vacuum (200 mbar) at room temperature for approximately 25 h. The resulting solid material was analyzed as described in Table 1.

The characteristic XRPD peaks of this 1,4-dioxane/toluene mixed solvate are as follows:

| 2-theta (°) | Relative intensity (%) |
|---|---|
| 6.69 | 62 |
| 10.86 | 82 |
| 18.34 | 100 |
| 19.40 | 72 |
| 21.38 | 67 |
| 23.76 | 62 |

15(l) 1,2-Dimethoxyethane/Toluene Mixed Solvate:

A saturated solution of compound of formula (I), Form VI in 1,2-dimethoxyethane was made at room temperature by adding 1.4 mL of 1,2-dimethoxyethane to approximately 698 mg of Form VI. The saturated solution was stirred for approximately 1 h and subsequently filtered through a filter of 0.45 μm pore size. A reverse addition of 2004 of the as prepared saturated solution was added at once to 800 μL of toluene acting as anti-solvent. After precipitation the solid material was separated from solution and dried under vacuum (200 mbar) at room temperature for approximately 25 h. The resulting solid material was analyzed as described in Table 1.

The characteristic XRPD peaks of this 1,2-dimethoxyethane/toluene mixed solvate are as follows:

| 2-theta (°) | Relative intensity (%) |
|---|---|
| 6.84 | 67 |
| 10.86 | 100 |
| 18.41 | 99 |
| 19.42 | 86 |
| 21.42 | 85 |
| 23.82 | 67 |

15(m) Methylbutyrate Solvate:

Approximately 24 mg of compound of formula (I), Form VI, was dissolved in 1 mL of methylbutyrate at room temperature. The solution was stirred at room temperature for 3 h. The solvent was then evaporated under vacuum (200 mbar) at room temperature, for approximately 115 h. The resulting solid material was analyzed as described in Table 1.

The characteristic XRPD peaks of this Methylbutyrate solvate are as follows:

| 2-theta (°) | Relative intensity (%) |
|---|---|
| 6.84 | 17 |
| 10.87 | 100 |
| 18.30 | 61 |
| 19.34 | 85 |
| 21.33 | 60 |
| 23.65 | 41 |

* Due to the preferred orientation affecting the relative intensity (%), their values were not considered in Table 6 defining the general characteristic XRPD peaks relative intensities of the isomorphic class 2.

Crystalline solvates of the kind described in this example have cavities which occupy between 3.3%-18.5% of the unit cell volume and which are accessible by solvent molecules. The approximate size of the cavity space was calculated using virtual solvent-free structures (by excluding the solvent molecules from the determined crystal structures in Table 3-5 and keeping the unit cell parameters unmodified). There is no particular limitation on the organic solvent which might be present within the cavity, other than that the resulting solvate be a crystalline solid. The solvent may be a single solvent, a mixture of solvents or an aqueous mixture containing the solvents. The solvent is typically the solvent used to manufacture crystalline compound of formula (I) or a pharmaceutical composition containing the compound of formula (I).

Table 6 sets forth the peak positions and relative peak intensity intervals for class 2 isomorphic solvates described in this example.

TABLE 1

Thermal analysis (DSC and TGA), single crystal analysis, and X-ray powder diffraction (XRPD) analyses of the different phases of compound of formula (I)

Figure 3:
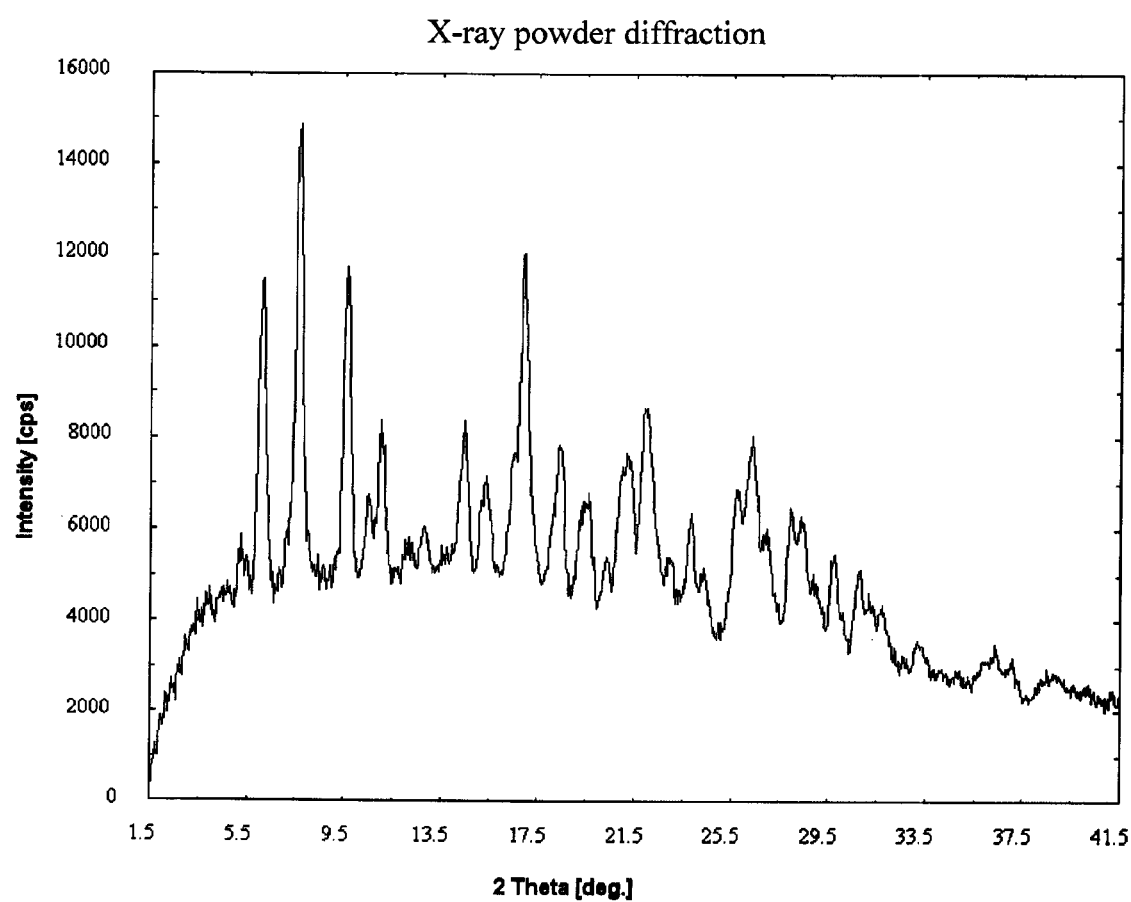
FIG. 3 sets forth identifying data for monohydrate of the compound of Formula I, above, including X-ray powder diffraction pattern.
Figure 4:
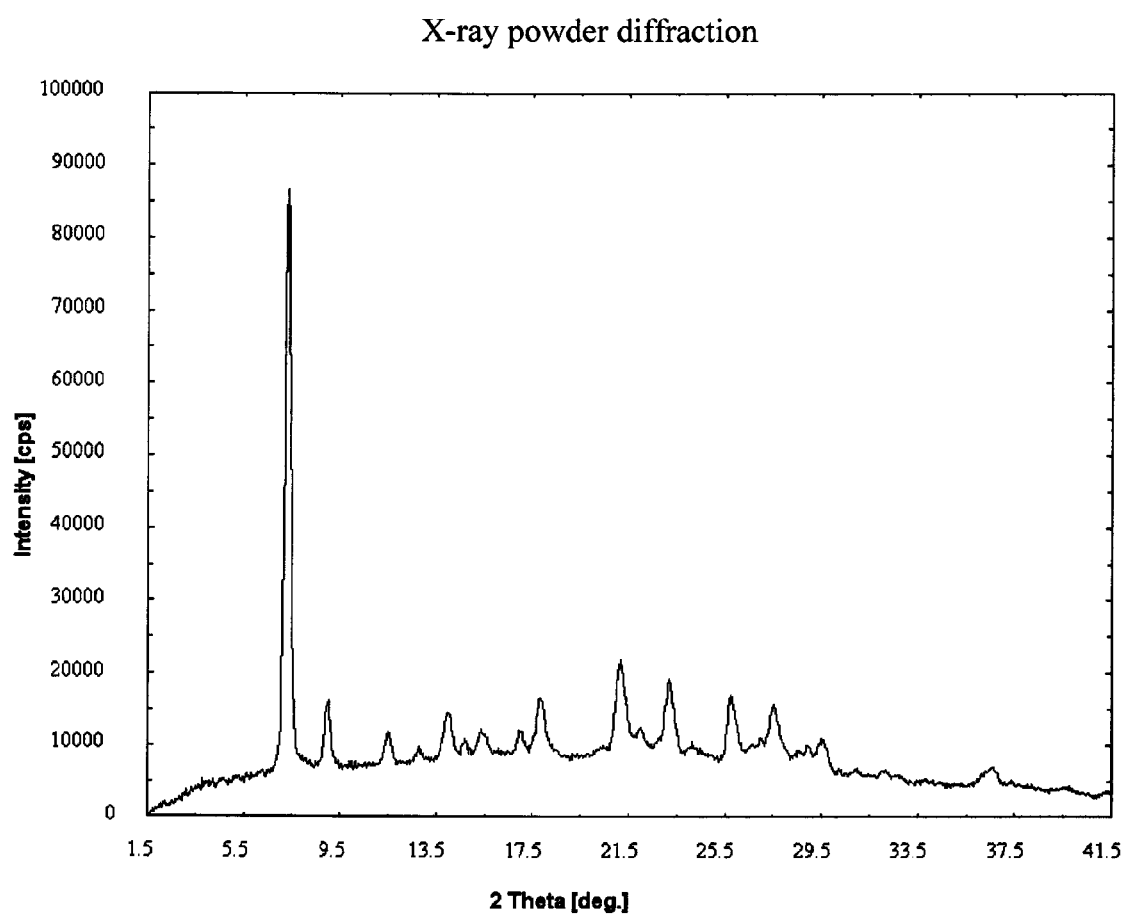
FIG. 4 sets forth identifying data for hydrate/methanol solvate 1 of the compound of Formula I, above, including X-ray powder diffraction pattern.
Figure 5:
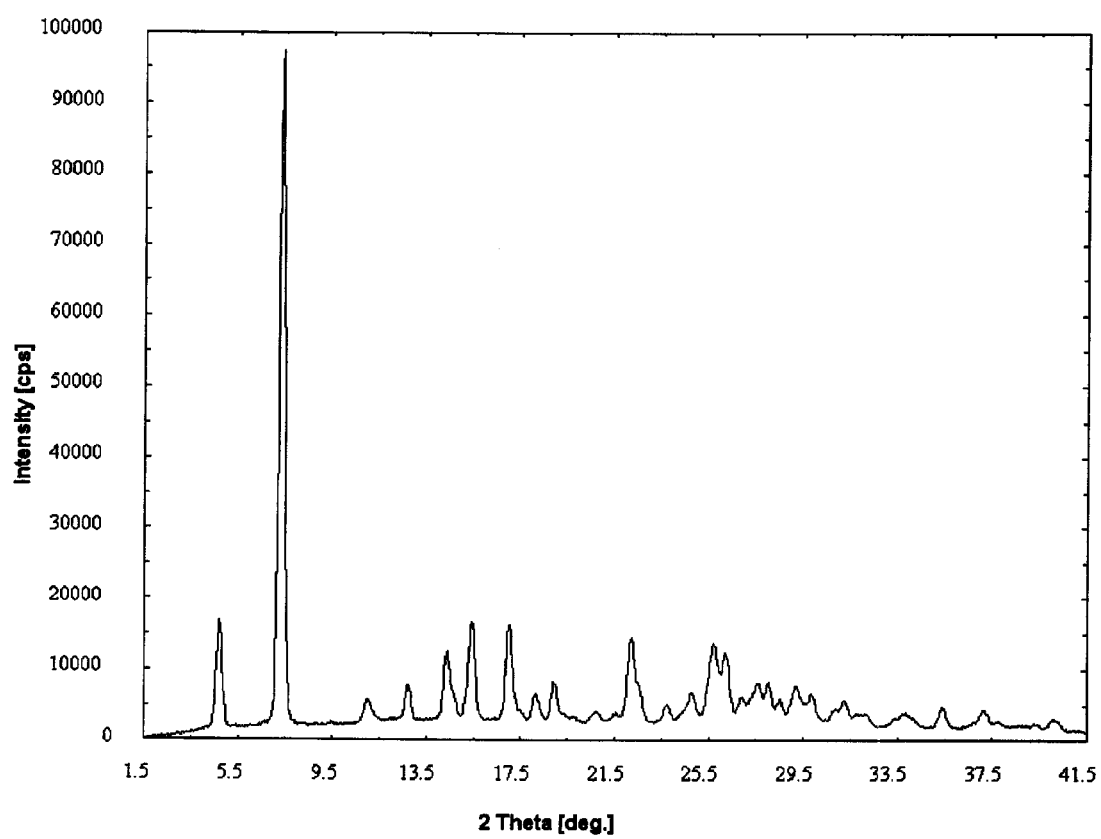
FIG. 5 sets forth identifying data for hydrate/ethyl formate solvate of the compound of Formula I, above, including X-ray powder diffraction pattern.

| Example No. | Form name | DSC ($T_{fus}$) | TGA (LOD) | Single crystal data | XRPD data[a] |
|---|---|---|---|---|---|
| 1 | Form VIII (anhydrate form) | | LOD = 3.46% | | FIG. 1 |
| 2 | Dihydrate | | LOD = 8.99% | | FIG. 2 |
| 3 | Monohydrate | | LOD = 5.02% | | FIG. 3 |
| 4 | Hydrate/methanol solvate 1 | $T_{fus}$ = 198° C. | LOD = 5% | | FIG. 4 |
| 5 | Hydrate/ethyl formate solvate | $T_{fus}$ = 110° C. | LOD = 11.59% | | FIG. 5 |

TABLE 1-continued

Thermal analysis (DSC and TGA), single crystal analysis, and X-ray powder diffraction (XRPD) analyses of the different phases of compound of formula (I)

Figure 6:
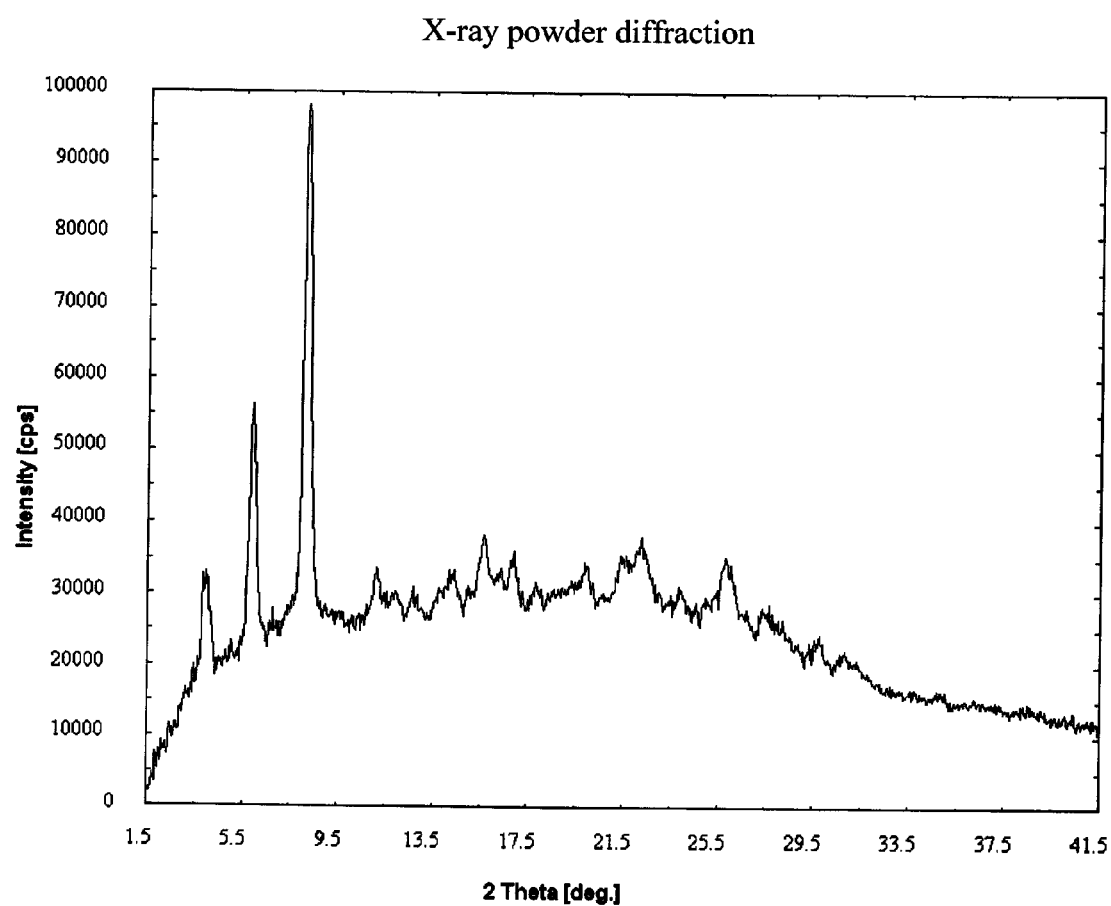
FIG. 6 sets forth identifying data for hydrate/methanol solvate 2 of the compound of Formula I, above, including X-ray powder diffraction pattern.
Figure 7:
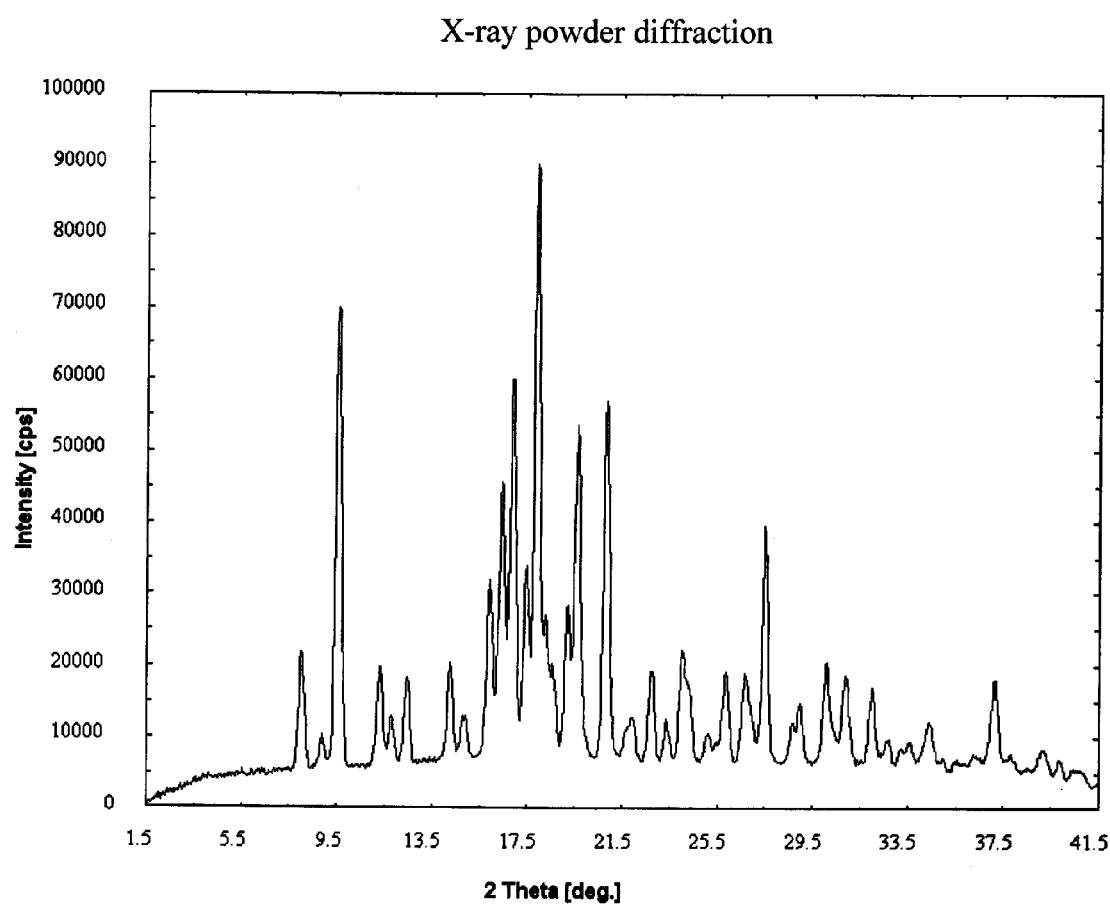
FIG. 7 sets forth identifying data for t-butylmethyl ether solvate 1 of the compound of Formula I, above, including X-ray powder diffraction pattern.
Figure 8:
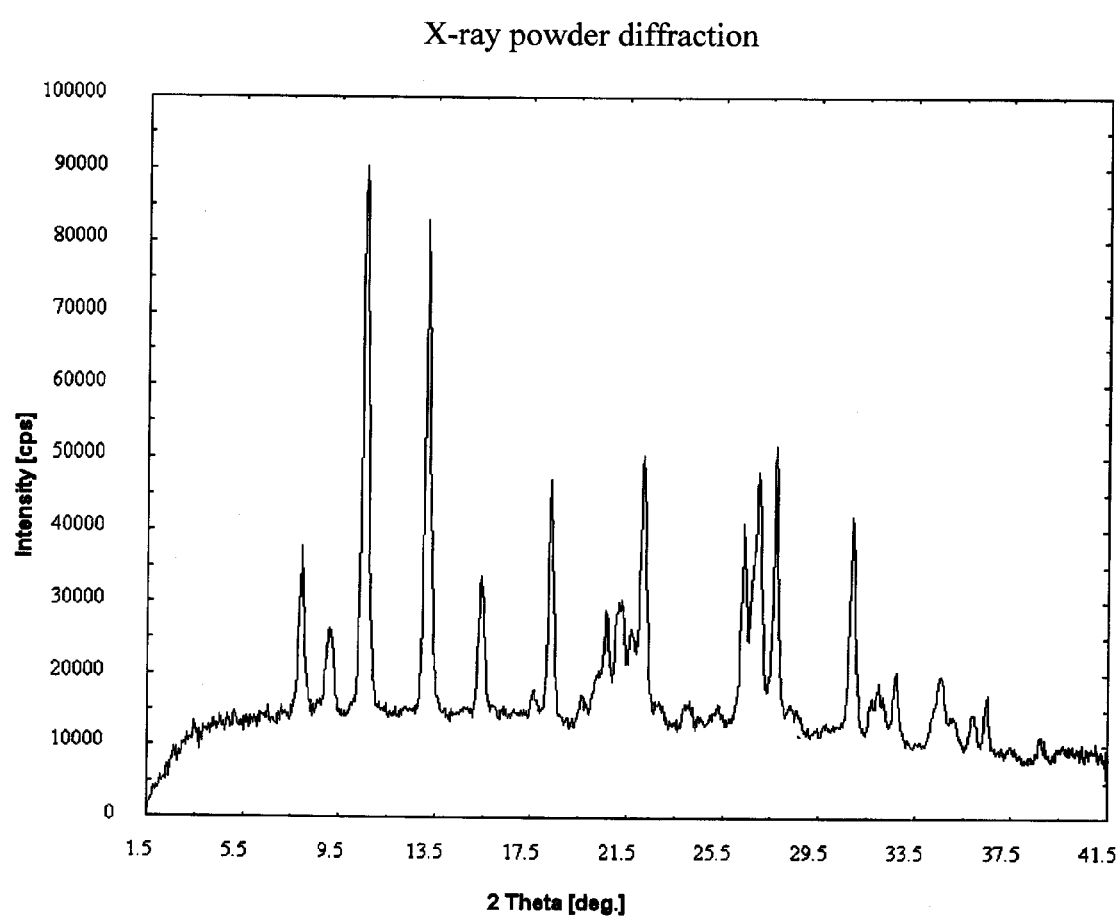
FIG. 8 sets forth identifying data for acetonitrile of the compound of Formula I, above, including X-ray powder diffraction pattern.
Figure 9:
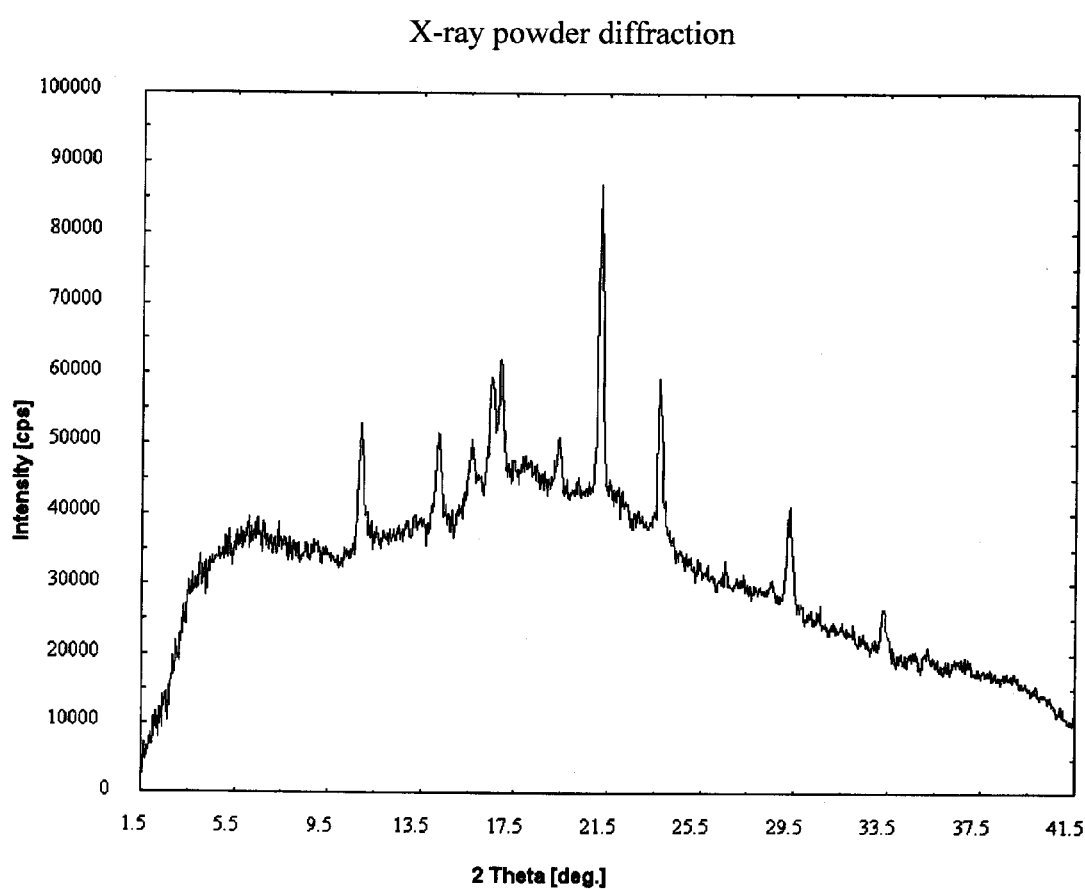
FIG. 9 sets forth identifying data for t-butylmethyl ether solvate 2 of the compound of Formula I, above, including X-ray powder diffraction pattern.
Figure 10:
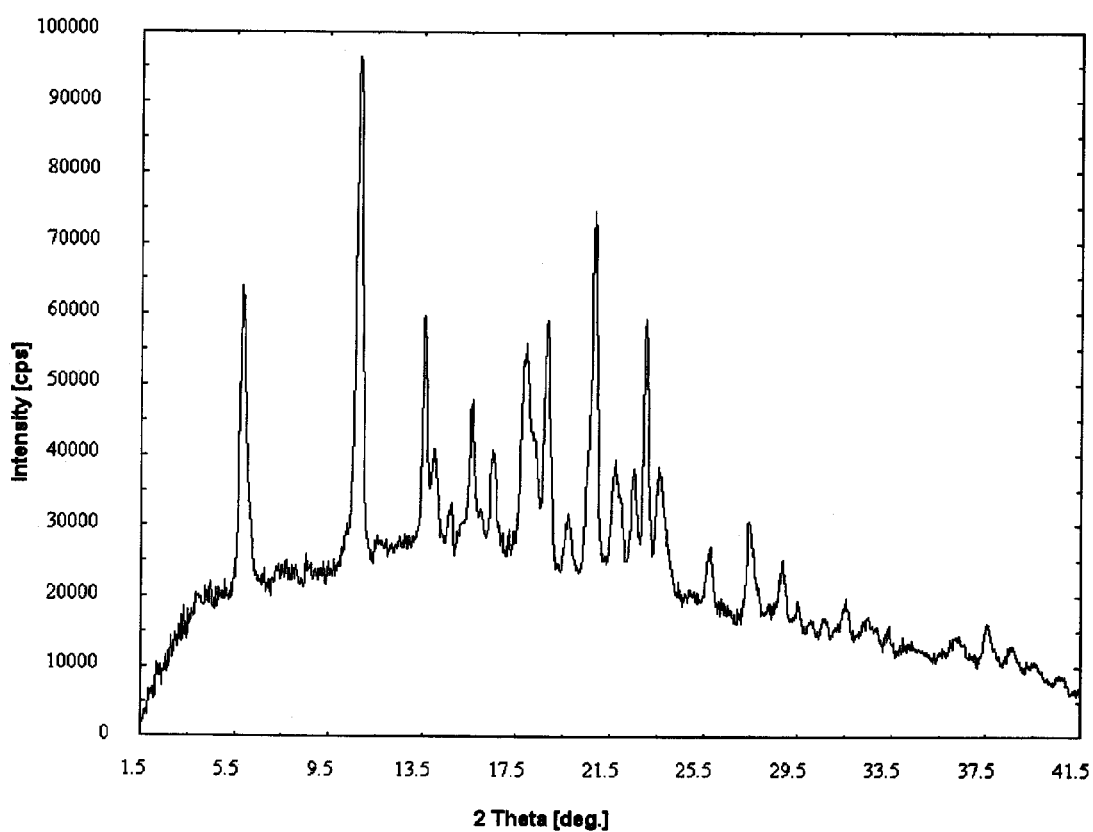
FIG. 10 sets forth identifying data for n-butyl acetate solvate of the compound of Formula I, above, including X-ray powder diffraction pattern.
Figure 11:
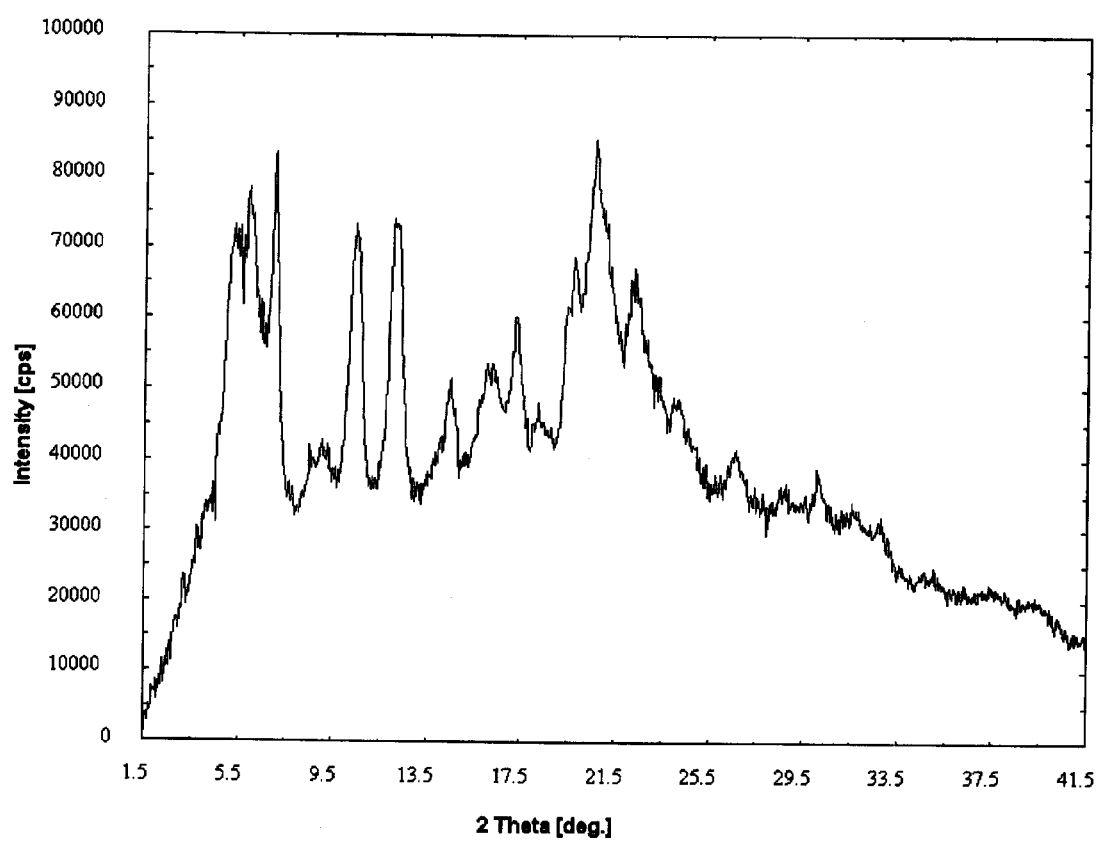
FIG. 11 sets forth identifying data for isopropyl ether solvate of the compound of Formula I, above, including X-ray powder diffraction pattern.
Figure 12:
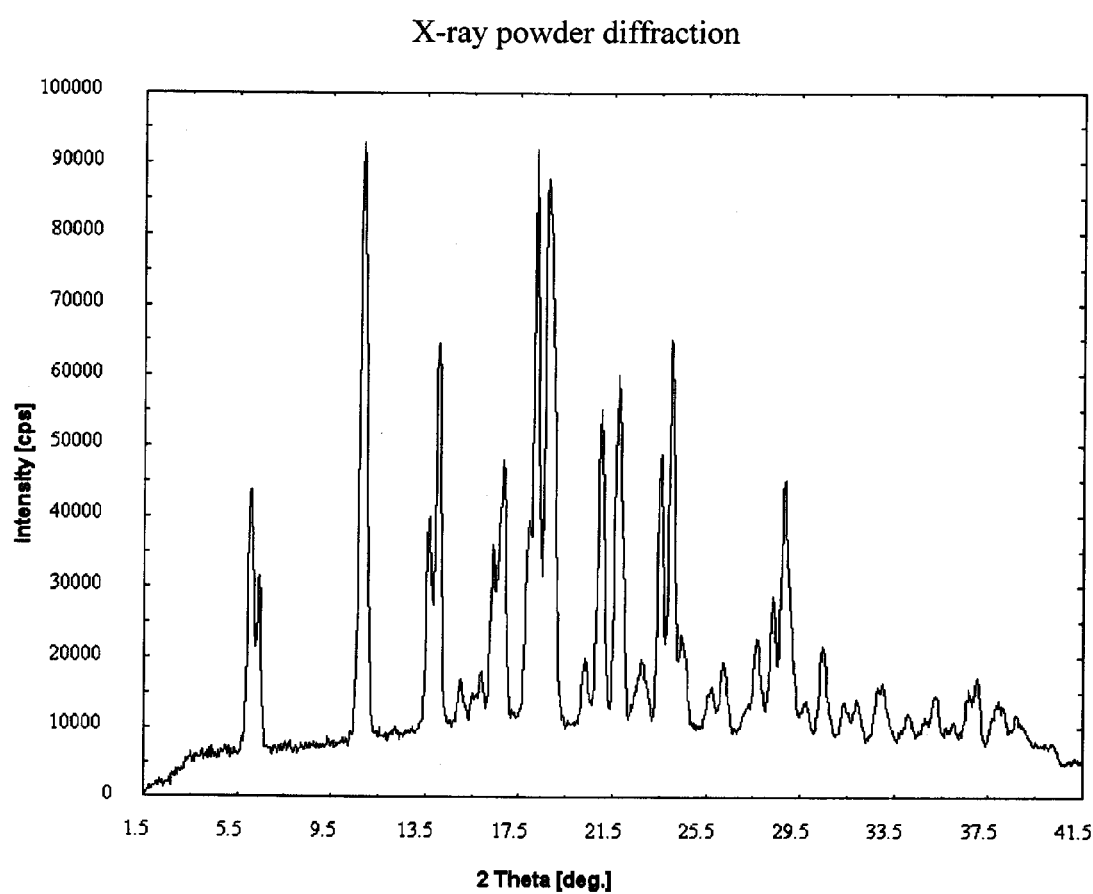
FIG. 12 sets forth identifying data for 1,2-dimethoxyethane/toluene solvate of the compound of Formula I, above, including X-ray powder diffraction pattern.
Figure 13:
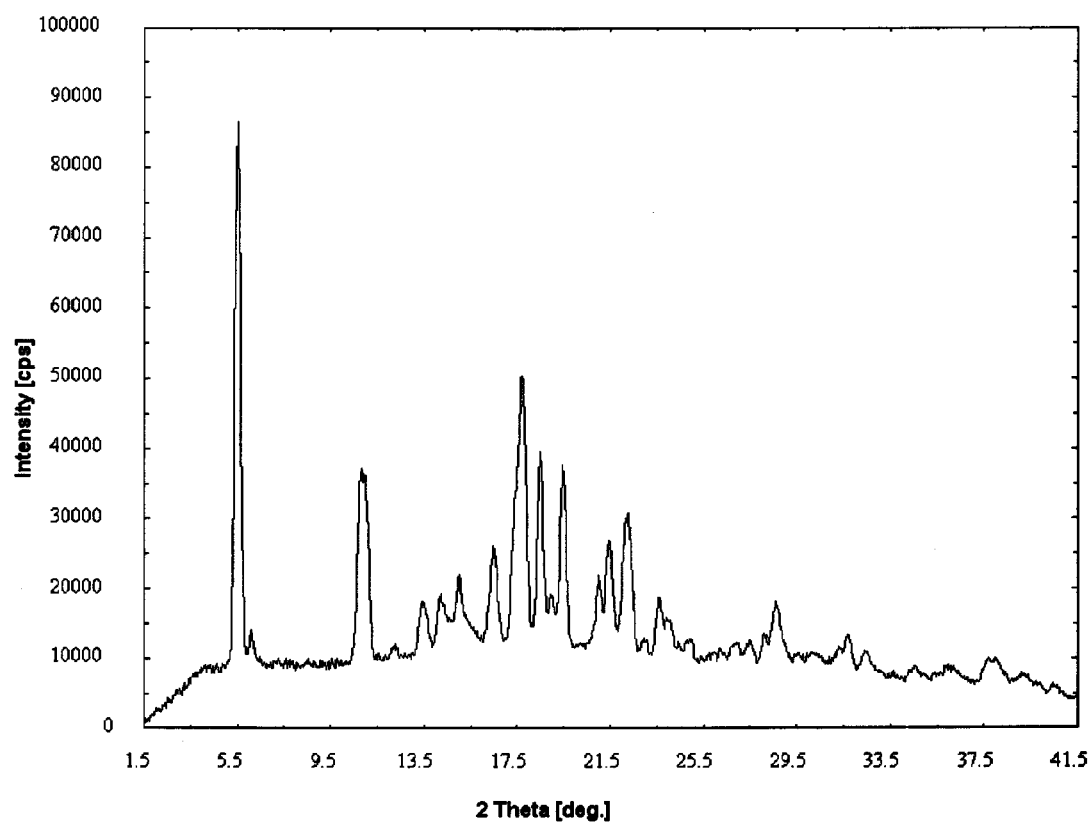
FIG. 13 sets forth identifying data for 2,2-dimethyl-3-butanone solvate of the compound of Formula I, above, including X-ray powder diffraction pattern.
Figure 14A:
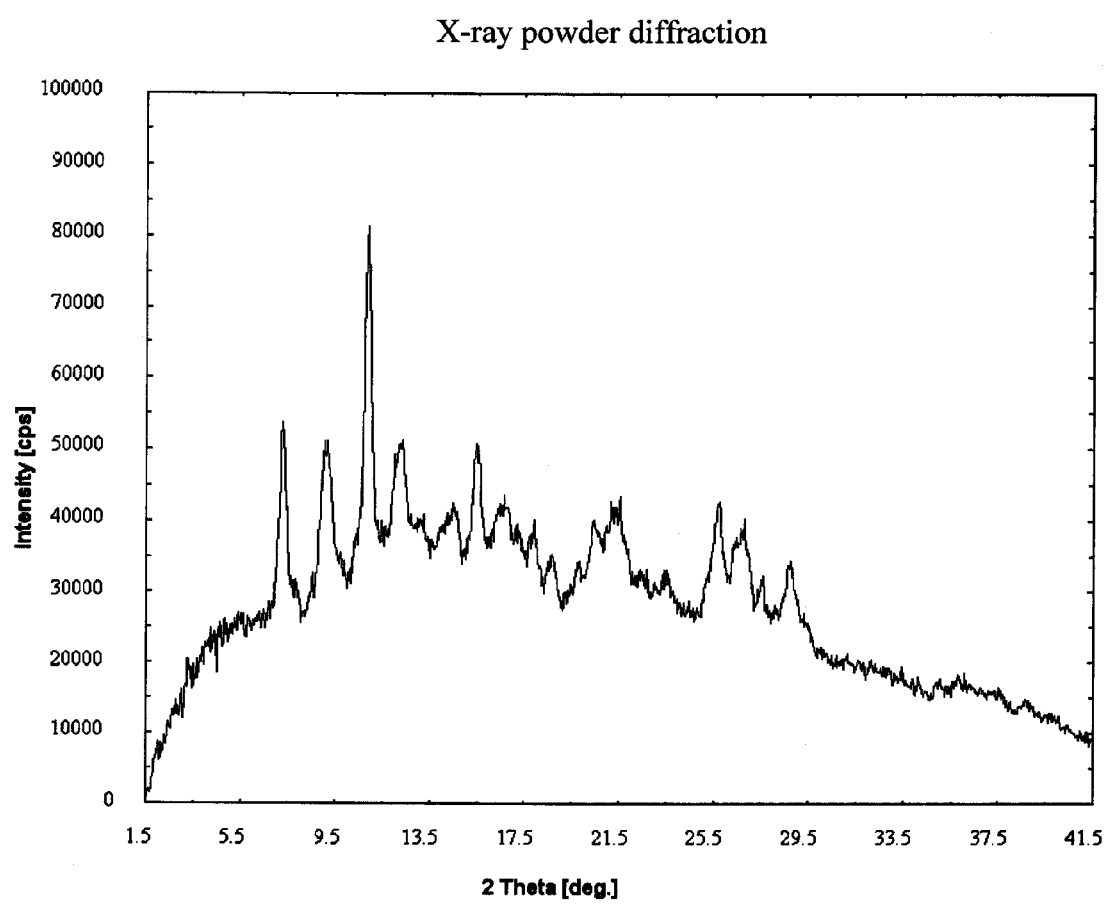
FIG. 14 sets forth identifying data for a group of isomorphic solvates of the compound of Formula I, above, including hexafluorobenzene solvate whose X-ray powder diffraction pattern is shown in FIG. 14A; and nitrobenzene solvate whose X-ray powder diffraction pattern is shown in FIG. 14B.
Figure 14B:
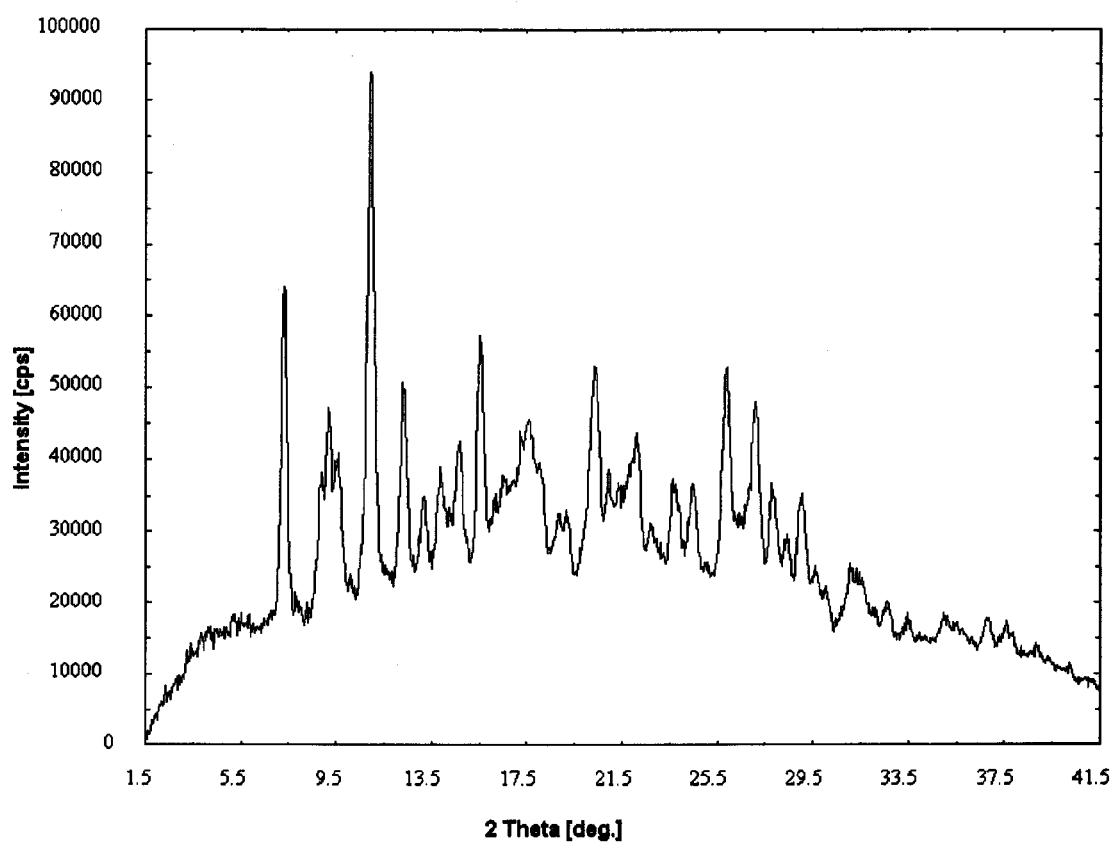

| Example No. | Form name | DSC ($T_{fus}$) | TGA (LOD) | Single crystal data | XRPD data[a] |
|---|---|---|---|---|---|
| 6 | Hydrate/methanol solvate 2 | | LOD = 5.9% | | FIG. 6 |
| 7 | t-butylmethyl ether solvate 1 | | LOD = 18.50% | | FIG. 7 |
| 8 | Acetonitrile solvate | $T_{fus}$ = 192° C. | LOD = 3% | | FIG. 8 |
| 9 | t-butylmethyl ether solvate 2 | | LOD = 11.29% (of a mixture with Form VI) | | FIG. 9 |
| 10 | n-butyl acetate solvate | | LOD = 9.08% | | FIG. 10 |
| 11 | Isopropyl ether solvate | $T_{fus}$ = 198° C. | LOD = 10.33% | | FIG. 11 |
| 12 | 1,2-dimethoxy ethane/toluene solvate | | LOD = 14.26% | | FIG. 12 |
| 13 | 2,2-dimethyl-3-butanone solvate | | LOD = 17.14% | | FIG. 13 |
| 14(a) | hexafluorobenzene solvate (Isomorphic class 1) | $T_{fus}$ = 197° C. | LOD = 16.48% | | FIG. 14A |
| 14(b) | NO$_2$-benzene solvate (Isomorphic class 1) | | LOD = 12.69% | | FIG. 14B |
| 15(a) | 1,4-dioxane solvate, (Isomorphic class 2) | | LOD = 16.50% | | FIG. 15A |
| 15(b) | THF solvate (Isomorphic class 2) | | | Table 3 (THF solvate) | FIG. 15B |
| 15(c) | Ethyl acetate/n-heptane mixed solvate, (Isomorphic class 2) | | LOD = 10.70% | | FIG. 15C |
| 15(d) | Ethyl acetate solvate (Isomorphic class 2) | | | Table 4 (ethyl acetate solvate) | FIG. 15D |
| 15(e) | n-propyl acetate solvate #1 (Isomorphic class 2) | | | | FIG. 15E |
| 15(f) | Ethyl acetate/cyclohexane solvate (Isomorphic class 2) | | LOD = 11.5% | | FIG. 15F |
| 15(g) | Ethyl actetate/toluene, solvate (Isomorphic class 2) | | | | FIG. 15G |
| 15(h) | isopropyl acetate, solvate (Isomorphic class 2) | | | Table 5 (isopropyl acetate solvate) | FIG. 15H2 |
| 15(i) | n-Propyl acetate solvate #2 (Isomorphic class 2) | | | | FIG. 15I |
| 15(j) | 1,4 dioxane/n-heptane solvate (Isomorphic class 2) | | LOD = 8.4% | | FIG. 15J |
| 15(k) | 1,4 dioxane/toluene solvate (Isomorphic class 2) | | | | FIG. 15K |
| 15(l) | 1,2-dimethoxyethane/toluene solvate (Isomorphic class 2) | | LOD = 6.6% | | FIG. 15L |
| 15(m) | Methylbutyrate solvate (Isomorphic class 2) | | | | FIG. 15M |

LOD = Loss on drying up to the melting or decomposition events
$T_{fus}$ = melting point
nd = not determined
[a] the X-ray powder diffraction pattern was obtained using a diffractometer equipped with a Hi-Star area detector using monochromatic CuKα radiation.

TABLE 2

Characteristic XRPD Peaks of Class 1 Isomorphic Solvates

| Peak position interval (2-theta °) | Relative Intensity interval (%)* |
|---|---|
| 7.2-7.3 | 65-70 |
| 9.1-9.2 | 50-65 |
| 10.8-11.0 | 100 |
| 12.2-12.4 | 50-70 |
| 15.4-15.6 | 50-70 |

*The peak positions and relative intensities vary as a function of the solvent embedded in the crystal structure.
** Extracted from the measured XRPD patterns, background not subtracted.

TABLE 3

Crystal and Structure Refinement of the THF Solvate from Isomorphic Class 2

| | |
|---|---|
| Empirical formula | $C_{15}H_{19}Cl_2N_3O_4 \cdot C_4H_8O$ |
| Formula weight | 448.34 |
| Temperature (K) | 293(2) |
| Wavelength (Å) | 0.71073 |
| Crystal system | Monoclinic |
| Space group | P 2$_1$ |
| Unit cell dimensions | |
| a [Å] | 16.321(2) |
| b [Å] | 9.641(2) |
| c [Å] | 16.683(2) |
| β [°] | 117.668(11) |
| V [Å$^3$] | 2324.9(6) |
| Z | 4 |
| $D_c$ [g/cm$^3$] | 1.281 |
| μ [mm$^{-1}$] | 0.312 |
| F(000) | 944 |
| Crystal size | 0.45 × 0.4 × 0.35 |
| Theta range for data collection (°) | 2.4 to 27.5 |
| Reflections collected | 14929 |
| Independent reflections | 10347 [$R_{int}$ = 0.0187] |
| Goodness-of-fit on F$^2$ | 1.039 |
| Final R indices [I > 2sigma(I)] | R1 = 0.0608, wR2 = 0.1620 |
| R indices (all data) | R1 = 0.0751, wR2 = 0.1785 |

TABLE 4

Crystal and Structure Refinement of the Ethylacetate Solvate from Isomorphic Class 2

| | |
|---|---|
| Empirical formula | $C_{15}H_{19}Cl_2N_3O_4 \cdot 0.5\ C_3H_6O_2$ |
| Formula weight | 413.27 |
| Temperature (K) | 293(2) |
| Wavelength (Å) | 0.71073 |
| Crystal system | Monoclinic |
| Space group | P 2$_1$ |
| Unit cell dimensions | |
| a [Å] | 16.331(3) |
| b [Å] | 9.828(2) |
| c [Å] | 16.816(4) |
| β [°] | 116.948(12) |
| V [Å$^3$] | 2405.9(9) |
| Z | 4 |
| $D_c$ [g/cm$^3$] | 1.141 |
| μ [mm$^{-1}$] | 0.296 |
| F(000) | 864 |
| Crystal size | 0.42 × 0.35 × 0.10 |
| Theta range for data collection | 2.5 to 27.5 |
| Reflections collected | 16599 |
| Independent reflections | 10709 [$R_{int}$ = 0.0397] |
| Goodness-of-fit on F$^2$ | 1.090 |
| Final R indices [I > 2σ(I)] | R1 = 0.0866, wR2 = 0.2239 |
| R indices (all data) | R1 = 0.1275, wR2 = 0.2544 |

TABLE 5

Crystal and Structure Refinement of the Isopropyl Acetate Solvate from Isomorphic Class 2

| | |
|---|---|
| Empirical formula | $C_{15}H_{19}Cl_2N_3O_4 \cdot 0.5\ C_5H_{10}O_2$ |
| Formula weight | 427.30 |
| Temperature (K) | 293(2) |
| Wavelength (Å) | 0.71073 |
| Crystal system | Monoclinic |
| Space group | P 2$_1$ |
| Unit cell dimensions | |
| a [Å] | 16.446(3) |
| b [Å] | 9.808(2) |
| c [Å] | 16.974(4) |
| β [°] | 117.873(16) |
| V [Å$^3$] | 2420.3(9) |
| Z | 4 |
| $D_c$ [g/cm$^3$] | 1.173 |
| F(000) | 896 |
| Crystal size | 0.45 × 0.35 × 0.15 |
| Theta range for data collection (°) | 2.5 to 27.5 |
| Reflections collected | 11708 |
| Independent reflections | 9102 [$R_{int}$ = 0.0352] |
| Goodness-of-fit on F$^2$ | 1.101 |
| Final R indices [I > 2σ(I)] | R1 = 0.0980, wR2 = 0.2522 |
| R indices (all data) | R1 = 0.1205, wR2 = 0.2782 |

TABLE 6

Isomorphic Characteristic XRPD Peaks of Class 2 Isomorphic Solvates

| Peak position interval (2-theta °)* | Relative Intensity interval (%)*,** |
|---|---|
| 5.9-6.9 | 48-68 |
| 10.8-11.0 | 60-100 |
| 18.0-18.5 | 80-100 |
| 19.0-19.5 | 55-90 |
| 21.0-21.5 | 40-85 |
| 23.4-23.8 | 35-75 |

*The peak positions and relative intensities vary as a function of the solvent embedded in the crystal structure.
**Extracted from the measured XRPD patterns, background not subtracted.

Several patent documents are cited in the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims. Furthermore, the transitional terms "comprising", "consisting essentially of" and "consisting of" define the scope of the appended claims, in original and amended form, with respect to what unrecited additional claim elements or steps, if any, are excluded from the scope of the claims. The term "comprising" is intended to be inclusive or open-ended and does not exclude additional, unrecited elements, methods step or materials. The phrase "consisting of" excludes any element, step or material other than those specified in the claim, and, in the latter instance, impurities ordinarily associated with the specified materials. The phrase "consisting essentially of" limits the scope of a claim to the specified elements, steps or materials and those that do not materially affect the basic and novel characteristic(s) of the claimed invention. All compositions or formulations identified herein can, in alternate embodiments, be more specifically defined by any of the transitional phases "comprising", "consisting essentially of" and "consisting of".

What is claimed is:

1. Crystalline Form VIII of 5,6-dichloro-2-(isopropylamino)-1-(β-L-ribofuranosyl)-1H-benzimidazole having an X-ray powder diffraction pattern substantially as shown in FIG. 1.

2. A crystalline form of 5,6-dichloro-2-(isopropylamino)-1-(β-L-ribofuranosyl)-1H-benzimidazole having an X-ray powder diffraction pattern selected from the group consisting of those substantially as shown in FIGS. 2-15.

3. A crystalline solvate form of 5,6-dichloro-2-(isopropylamino)-1-(β-L-ribofuranosyl)-1H-benzimidazole, including a stoichiometric ratio of an organic solvent within at least one cavity of the crystal lattice, said solvent being selected from the group of methanol, ethyl formate, t-butylmethyl ether, acetonitrile, ethyl acetate, n-propyl acetate, isopropyl acetate, n-butyl acetate, isopropyl ether, 1,2-dimethoxyethane, toluene, 2,2-dimethyl-3-butanone, hexafluorbenzene, nitrobenzene, 1,4-dioxane, tetrahydrofuran (THF), n-heptane, cyclohexane, methylbutyrate, or mixtures thereof.

4. A pharmaceutical composition comprising a crystalline form of 5,6-dichloro-2-(isopropylamino)-1-(β-L-ribofuranosyl)-1H-benzimidazole according to claim 1 and at least one pharmaceutically acceptable carrier.

5. A pharmaceutical composition according to claim 4 in the form of a powder, tablet, capsule or suspension.

6. A composition comprising an admixture of crystalline Form VIII of 5,6-dichloro-2-(isopropylamino)-1-(β-L-ribofuranosyl)-1H-benzimidazole, together with at least one of Form I, Form II, ethanol solvate, Form IV, Form V, Form VI and amorphous 5,6-dichloro-2-(isopropylamino)-1-(β-L-ribofuranosyl)-1H-benzimidazole.

7. A composition comprising an admixture of a crystalline form of 5,6-dichloro-2-(isopropylamino)-1-(β-L-ribofuranosyl)-1H-benzimidazole according to claim 2 together with at least one of Form I, Form II, ethanol solvate, Form IV, Form V, Form VI and amorphous 5,6-dichloro-2-(isopropylamino)-1-(β-L-ribofuranosyl)-1H-benzimidazole.

8. A method for treatment or prophylaxis of a herpes viral infection in a patient in need thereof comprising administering to said patient an effective anti-viral amount of crystalline Form VIII of 5,6-dichloro-2-(isopropylamino)-1-(β-L-ribofuranosyl)-1H-benzimidazole according to claim 1.

9. A method according to claim 8, wherein said herpes viral infection is cytomegalovirus (CMV).

10. A method for treatment or prophylaxis of a herpes viral infection in a patient in need thereof comprising administering to said patient an effective anti-viral amount of a crystalline form of 5,6-dichloro-2-(isopropylamino)-1-(β-L-ribofuranosyl)-1H-benzimidazole according to claim 2.

11. A method according to claim 10, wherein said herpes viral infection is cytomegalovirus (CMV).

12. The crystalline solvate of claim 3, wherein said cavity (or cavities) including said solvent or solvent mixture occupies between about 3.3 to about 18.5% of the unit cell volume.

13. The crystalline solvate of claim 12, wherein said cavity or cavities also includes water.

* * * * *